(12) United States Patent
Morrison et al.

(10) Patent No.: US 11,944,425 B2
(45) Date of Patent: *Apr. 2, 2024

(54) COMPLIANCE MONITORING MODULE FOR AN INHALER

(71) Applicant: Norton (Waterford) Limited, Waterford (IE)

(72) Inventors: Mark Steven Morrison, Basking Ridge, NJ (US); Douglas E. Weitzel, Hamilton, NJ (US); Enrique Calderon Oliveras, Waterford (IE); Daniel Buck, Waterford (IE)

(73) Assignee: Norton (Waterford) Limited, Waterford (IE)

( * ) Notice: Subject to any disclaimer, the term of this patent is extended or adjusted under 35 U.S.C. 154(b) by 479 days.

This patent is subject to a terminal disclaimer.

(21) Appl. No.: 17/148,991

(22) Filed: Jan. 14, 2021

(65) Prior Publication Data

US 2021/0128018 A1   May 6, 2021

Related U.S. Application Data

(63) Continuation of application No. 15/507,386, filed as application No. PCT/US2015/047369 on Aug. 28, 2015, now Pat. No. 10,905,356.

(Continued)

(51) Int. Cl.
*A61B 5/087* (2006.01)
*A61B 5/00* (2006.01)
(Continued)

(52) U.S. Cl.
CPC .............. *A61B 5/087* (2013.01); *A61B 5/097* (2013.01); *A61B 5/4833* (2013.01);
(Continued)

(58) Field of Classification Search
CPC ............ A61M 16/021; A61M 16/0051; A61M 15/00; A61M 15/009; A61M 15/0063; A61M 2209/088; A61M 2016/0027
See application file for complete search history.

(56) References Cited

U.S. PATENT DOCUMENTS

| 955,201 | A | 4/1910 | Rand |
| 4,984,158 | A | 1/1991 | Hillsman |

(Continued)

FOREIGN PATENT DOCUMENTS

| CN | 101176804 A | 5/2008 |
| EP | 667168 A1 | 8/1995 |

(Continued)

OTHER PUBLICATIONS

Kumar, et al., "Biomedical Applications Of Mems & Nems Pressure Transducers/ Sensors", International Journal of Innovative Research and Development, vol. 2. Issue 5, May 2013, pp. 1832-1841.

(Continued)

*Primary Examiner* — Michael R Reid
*Assistant Examiner* — Nathan M Le
(74) *Attorney, Agent, or Firm* — Flaster Greenberg P.C.

(57) ABSTRACT

A compliance monitoring module for an inhaler comprising: a miniature pressure sensor, a sensor port of said sensor being configured to be pneumatically coupled to a flow channel of said inhaler through which a user can inhale; a processor configured to: receive data from a sensing element of the pressure sensor; receive data from a mode sensor configured to detect when the inhaler changes from an inactive mode to an active mode; and based on said data from said pressure sensor sensing element and said data from said mode sensor, compile a compliance report; and a transmitter configured to issue said compliance report.

19 Claims, 11 Drawing Sheets

Related U.S. Application Data

(60) Provisional application No. 62/043,114, filed on Aug. 28, 2014.

(51) Int. Cl.
*A61B 5/097* (2006.01)
*A61M 15/00* (2006.01)
*A61M 16/00* (2006.01)
*G16H 20/10* (2018.01)

(52) U.S. Cl.
CPC ...... *A61M 16/0051* (2013.01); *A61M 16/021* (2017.08); *G16H 20/10* (2018.01); *A61B 2562/028* (2013.01); *A61B 2562/0285* (2013.01); *A61M 15/00* (2013.01); *A61M 15/009* (2013.01); *A61M 15/0096* (2014.02); *A61M 2016/0027* (2013.01); *A61M 16/0063* (2014.02); *A61M 2209/088* (2013.01)

(56) References Cited

U.S. PATENT DOCUMENTS

| | | |
|---|---|---|
| 5,071,453 A | 12/1991 | Hradek et al. |
| 5,363,842 A | 11/1994 | Mishelevich et al. |
| 5,505,192 A | 4/1996 | Samiotes et al. |
| 5,692,492 A | 12/1997 | Bruna et al. |
| 5,809,997 A | 9/1998 | Wolf |
| 5,839,429 A | 11/1998 | Marnfeldt et al. |
| 5,842,468 A | 12/1998 | Denyet et al. |
| 5,887,586 A | 3/1999 | Dahlback et al. |
| 5,957,125 A | 9/1999 | Sagstetter et al. |
| 6,148,815 A | 11/2000 | Wolf et al. |
| 6,283,923 B1 | 9/2001 | Finkelstein et al. |
| 6,285,731 B1 | 9/2001 | Marnfeldt et al. |
| 6,390,088 B1 | 5/2002 | Sprenger et al. |
| 6,446,627 B1 | 9/2002 | Bowman et al. |
| 6,651,651 B1 | 11/2003 | Bonney et al. |
| 6,693,546 B2 | 2/2004 | Skardon |
| 6,752,145 B1 | 6/2004 | Bonney et al. |
| 6,932,083 B2 | 8/2005 | Jones et al. |
| 6,958,691 B1 | 10/2005 | Anderson et al. |
| 6,978,780 B1 | 12/2005 | Marnfeldt et al. |
| 6,981,499 B2 | 1/2006 | Anderson et al. |
| 6,990,975 B1 | 1/2006 | Jones et al. |
| 7,072,738 B2 | 7/2006 | Bonney et al. |
| 7,151,456 B2 | 12/2006 | Godfrey et al. |
| 7,191,777 B2 | 3/2007 | Brand et al. |
| 7,198,172 B2 | 4/2007 | Harvey et al. |
| 7,233,228 B2 | 6/2007 | Lintell et al. |
| 7,249,687 B2 | 7/2007 | Anderson et al. |
| 7,347,200 B2 | 3/2008 | Jones et al. |
| 7,383,837 B2 | 6/2008 | Robertson et al. |
| 7,424,888 B2 | 9/2008 | Harvey et al. |
| 7,495,546 B2 | 2/2009 | Lintell et al. |
| 7,587,988 B2 | 9/2009 | Bowman et al. |
| 7,837,648 B2 | 11/2010 | Blair et al. |
| 8,231,541 B2 | 7/2012 | Colquitt et al. |
| 8,231,573 B2 | 7/2012 | Edwards et al. |
| 8,240,301 B2 | 8/2012 | Spaargaren et al. |
| 8,251,056 B2 | 8/2012 | Pearson et al. |
| 8,342,172 B2 | 1/2013 | Levy et al. |
| 8,403,865 B2 | 3/2013 | Halperin et al. |
| 8,424,517 B2 | 4/2013 | Sutherland et al. |
| 8,464,707 B2 | 6/2013 | Jongejan et al. |
| 8,491,493 B2 | 7/2013 | Colquitt et al. |
| 8,547,239 B2 | 10/2013 | Peatfield et al. |
| 8,620,591 B2 | 12/2013 | Wegerich |
| 8,758,262 B2 | 6/2014 | Rhee et al. |
| 8,795,170 B2 | 8/2014 | Pipke |
| 8,807,131 B1 | 8/2014 | Tunnell et al. |
| 8,960,189 B2 | 2/2015 | Morrison et al. |
| 8,978,966 B2 | 3/2015 | Walsh et al. |
| 8,997,735 B2 | 4/2015 | Zierenberg et al. |
| 9,056,174 B2 | 6/2015 | Bradshaw et al. |
| 9,174,009 B2 | 11/2015 | Peatfield et al. |
| 9,188,579 B2 | 11/2015 | Shen et al. |
| 9,237,862 B2 | 1/2016 | Bussa et al. |
| 9,242,056 B2 | 1/2016 | Andersen et al. |
| 9,265,445 B2 | 2/2016 | Shinar et al. |
| 9,339,616 B2 | 5/2016 | Denny et al. |
| 9,364,619 B2 | 6/2016 | Overfield et al. |
| 9,427,534 B2 | 8/2016 | Bruin et al. |
| 9,463,291 B2 | 10/2016 | Imran et al. |
| 9,468,729 B2 | 10/2016 | Sutherland et al. |
| 9,550,031 B2 | 1/2017 | Van Sickle et al. |
| 9,555,200 B2 | 1/2017 | Hosemann et al. |
| 9,555,201 B2 | 1/2017 | Collins et al. |
| 9,638,084 B2 | 5/2017 | Saiki |
| 9,694,147 B2 | 7/2017 | Peatfield et al. |
| 9,736,642 B2 | 8/2017 | Ostrander et al. |
| 9,782,551 B2 | 10/2017 | Morrison et al. |
| 9,839,398 B2 | 12/2017 | Yamamori et al. |
| 9,911,308 B2 | 3/2018 | Edwards et al. |
| 9,956,360 B2 | 5/2018 | Germinario et al. |
| 9,962,507 B2 | 5/2018 | Germinario et al. |
| 9,962,508 B2 | 5/2018 | Bruin et al. |
| 10,016,134 B2 | 7/2018 | Hansen et al. |
| 10,046,121 B2 | 8/2018 | Kolb et al. |
| 10,255,412 B2 | 4/2019 | Hogg et al. |
| 10,363,384 B2 | 7/2019 | Dyche et al. |
| 10,406,305 B2 | 9/2019 | Collins et al. |
| 10,531,838 B2 | 1/2020 | Barretto et al. |
| 10,556,070 B2 | 2/2020 | Van Sickle et al. |
| 10,664,572 B2 | 5/2020 | Bitran et al. |
| 10,726,954 B2 | 7/2020 | Su et al. |
| 10,810,283 B2 | 10/2020 | Shetty et al. |
| 10,849,314 B2 | 12/2020 | Genzow et al. |
| 10,905,356 B2* | 2/2021 | Morrison ............... A61B 5/097 |
| 2002/0185128 A1 | 12/2002 | Theobald et al. |
| 2003/0192535 A1 | 10/2003 | Christrup et al. |
| 2003/0205229 A1 | 11/2003 | Crockford et al. |
| 2004/0089299 A1 | 5/2004 | Bonney et al. |
| 2004/0117062 A1 | 6/2004 | Bonney et al. |
| 2005/0043674 A1 | 2/2005 | Blair et al. |
| 2005/0076904 A1 | 4/2005 | Jones et al. |
| 2005/0119604 A1 | 6/2005 | Bonney et al. |
| 2005/0161467 A1 | 7/2005 | Jones et al. |
| 2005/0172958 A1 | 8/2005 | Singer et al. |
| 2005/0247312 A1 | 11/2005 | Davies et al. |
| 2005/0251289 A1 | 11/2005 | Bonney et al. |
| 2006/0254581 A1 | 11/2006 | Genova et al. |
| 2007/0017506 A1 | 1/2007 | Bell et al. |
| 2007/0251950 A1 | 11/2007 | Bacon |
| 2007/0295329 A1 | 12/2007 | Lieberman et al. |
| 2008/0173301 A1 | 7/2008 | Deaton et al. |
| 2008/0178872 A1 | 7/2008 | Genova et al. |
| 2008/0230057 A1 | 9/2008 | Sutherland et al. |
| 2009/0151718 A1 | 6/2009 | Hunter et al. |
| 2009/0151723 A1 | 6/2009 | Lang et al. |
| 2009/0194104 A1 | 8/2009 | Van Sickle |
| 2009/0221308 A1 | 9/2009 | Lerner et al. |
| 2010/0036266 A1 | 2/2010 | Nysaether et al. |
| 2010/0094099 A1 | 4/2010 | Levy et al. |
| 2010/0242960 A1 | 9/2010 | Zangerle et al. |
| 2010/0250280 A1 | 9/2010 | Sutherland et al. |
| 2011/0041845 A1 | 2/2011 | Solomon et al. |
| 2011/0226242 A1 | 9/2011 | Von Hollen et al. |
| 2011/0253139 A1 | 10/2011 | Guthrie et al. |
| 2011/0282693 A1 | 11/2011 | Craft et al. |
| 2011/0283997 A1 | 11/2011 | Walsh et al. |
| 2013/0008436 A1 | 1/2013 | Von Hollen et al. |
| 2013/0053719 A1 | 2/2013 | Wekell |
| 2013/0151162 A1 | 6/2013 | Harris et al. |
| 2013/0239957 A1 | 9/2013 | Pinfold |
| 2013/0269685 A1 | 10/2013 | Wachtel et al. |
| 2013/0298905 A1 | 11/2013 | Levin et al. |
| 2014/0106324 A1 | 4/2014 | Adams et al. |
| 2014/0182584 A1 | 7/2014 | Sutherland et al. |
| 2014/0264653 A1 | 9/2014 | Cheng et al. |
| 2014/0305429 A1 | 10/2014 | Lewis |
| 2015/0061867 A1* | 3/2015 | Engelhard ........... A61M 15/009 |
| | | 340/539.18 |
| 2015/0150484 A1 | 6/2015 | Wekell |
| 2015/0174348 A1 | 6/2015 | Tunnell et al. |

(56) References Cited

U.S. PATENT DOCUMENTS

| | | |
|---|---|---|
| 2015/0283341 A1 | 10/2015 | Adams et al. |
| 2016/0082208 A1 | 3/2016 | Ballam et al. |
| 2016/0089089 A1 | 3/2016 | Kakkar et al. |
| 2016/0128389 A1 | 5/2016 | Lamb et al. |
| 2016/0129182 A1 | 5/2016 | Schuster et al. |
| 2016/0144141 A1 | 5/2016 | Biswas et al. |
| 2016/0166766 A1 | 6/2016 | Schuster et al. |
| 2016/0228657 A1 | 8/2016 | Sutherland et al. |
| 2016/0256639 A1 | 9/2016 | Van Sickle et al. |
| 2016/0283686 A1 | 9/2016 | Hu et al. |
| 2016/0314256 A1 | 10/2016 | Su et al. |
| 2017/0079557 A1 | 3/2017 | Lauk et al. |
| 2017/0109493 A1 | 4/2017 | Hogg et al. |
| 2017/0140125 A1 | 5/2017 | Hogg et al. |
| 2017/0161461 A1 | 6/2017 | Delangre et al. |
| 2017/0164892 A1 | 6/2017 | Sezan et al. |
| 2017/0173279 A1 | 6/2017 | Sutherland et al. |
| 2017/0213145 A1 | 7/2017 | Pathak et al. |
| 2017/0246406 A1 | 8/2017 | Sutherland et al. |
| 2017/0258993 A1 | 9/2017 | Pizzochero et al. |
| 2017/0262613 A1 | 9/2017 | Ljungberg et al. |
| 2017/0325734 A1 | 11/2017 | Sutherland et al. |
| 2017/0363673 A1 | 12/2017 | Mukherjee et al. |
| 2018/0011988 A1 | 1/2018 | Ziegler et al. |
| 2018/0052964 A1 | 2/2018 | Adelson et al. |
| 2018/0056018 A1 | 3/2018 | Canvin et al. |
| 2018/0085540 A1 | 3/2018 | Dantsker et al. |
| 2018/0125365 A1 | 5/2018 | Hunter et al. |
| 2018/0161530 A1 | 6/2018 | Ganton et al. |
| 2018/0221600 A1 | 8/2018 | Shears et al. |
| 2019/0014824 A1 | 1/2019 | Yazbeck et al. |
| 2019/0030262 A1 | 1/2019 | Ziegler et al. |
| 2019/0102522 A1 | 4/2019 | Barrett et al. |
| 2019/0108912 A1 | 4/2019 | Spurlock et al. |
| 2019/0111222 A1 | 4/2019 | Wang et al. |
| 2019/0134330 A1 | 5/2019 | Germinario et al. |
| 2019/0189258 A1 | 6/2019 | Barrett et al. |
| 2019/0272925 A1 | 9/2019 | Barrett et al. |
| 2019/0290129 A1 | 9/2019 | Hanina et al. |
| 2019/0307648 A1 | 10/2019 | Bartos |
| 2019/0313919 A1 | 10/2019 | Pritchard et al. |
| 2019/0328278 A1 | 10/2019 | Zabel et al. |
| 2019/0385727 A1 | 12/2019 | Manice et al. |
| 2020/0003437 A1 | 1/2020 | Breen |
| 2020/0058403 A1 | 2/2020 | Barrett et al. |
| 2020/0098459 A1 | 3/2020 | Hanina et al. |
| 2020/0135334 A1 | 4/2020 | Rajasekhar et al. |
| 2020/0143939 A1 | 5/2020 | Semen et al. |
| 2020/0188613 A1 | 6/2020 | Van Sickle et al. |
| 2020/0193806 A1 | 6/2020 | Finke et al. |
| 2020/0250554 A1 | 8/2020 | Shao et al. |

FOREIGN PATENT DOCUMENTS

| | | |
|---|---|---|
| EP | 0667168 A1 | 8/1995 |
| EP | 1135056 B1 | 8/2006 |
| EP | 1992381 A1 | 11/2008 |
| EP | 3228345 A1 | 10/2017 |
| JP | H04500915 A | 2/1992 |
| JP | H11511676 A | 10/1999 |
| JP | 2002543935 A | 12/2002 |
| JP | 2003516199 A | 5/2003 |
| JP | 2009507540 A | 2/2009 |
| JP | 2013-516265 A | 5/2013 |
| JP | 2013532019 A | 8/2013 |
| JP | 2014513591 A | 6/2014 |
| WO | 8911823 | 12/1989 |
| WO | WO/1995/022365 A1 | 8/1995 |
| WO | 9638084 A1 | 12/1996 |
| WO | WO/1999/063901 A1 | 12/1999 |
| WO | WO 1999/064095 A2 | 12/1999 |
| WO | 0069496 A1 | 11/2000 |
| WO | 0141849 A2 | 6/2001 |
| WO | WO/2003/063754 A1 | 8/2003 |
| WO | 2005020023 A2 | 3/2005 |
| WO | 2007028992 A1 | 3/2007 |
| WO | WO/2009/003989 A1 | 1/2009 |
| WO | 2011010282 A1 | 1/2011 |
| WO | WO/2011/083377 A1 | 7/2011 |
| WO | 2011157561 A1 | 12/2011 |
| WO | 2012123448 A1 | 9/2012 |
| WO | 2013085910 A1 | 6/2013 |
| WO | 2013098714 A1 | 7/2013 |
| WO | WO/2016/043601 A1 | 3/2016 |
| WO | WO/2017/005605 A1 | 1/2017 |
| WO | WO/2017/051389 A1 | 3/2017 |
| WO | WO/2017/129521 A1 | 8/2017 |
| WO | WO/2017/141194 A1 | 8/2017 |
| WO | WO/2017/176693 A1 | 10/2017 |
| WO | WO/2017/176704 A1 | 10/2017 |
| WO | WO/2017/180980 A1 | 10/2017 |
| WO | 2017192778 A1 | 11/2017 |
| WO | WO/2017/189712 A1 | 11/2017 |
| WO | WO/2018/128976 A1 | 7/2018 |
| WO | WO2018/134552 A1 | 7/2018 |
| WO | WO/2018/134553 A1 | 7/2018 |
| WO | 2018160073 A1 | 9/2018 |
| WO | 2019022620 A1 | 1/2019 |
| WO | 2019226576 A1 | 11/2019 |

OTHER PUBLICATIONS

"Freescale Semiconductor Data Sheet", Data Sheet for the Freescale MPL31152A2 Altimeter, Rev 2.2, Jul. 2012, 44 pages.

Liu, Andrew, et al., "Advances in Asthma 2015: Across the Lifespan", Journal of Allergy and Clinical Immunology, Elsevier, Amsterdam, NL, vol. 138, No. 2., Aug. 3, 2016, pp. 397-404.

Safioti, Guilherme, et al., "A Predictive Model for Clinical Asthma Exacerbations Using Albuterol eMDPI (ProAir Digihaler): A Twelve-Week, Open-Label Study", ATS Annual Conference, Dallas, Texas, May 22, 2019, p. 693.

* cited by examiner

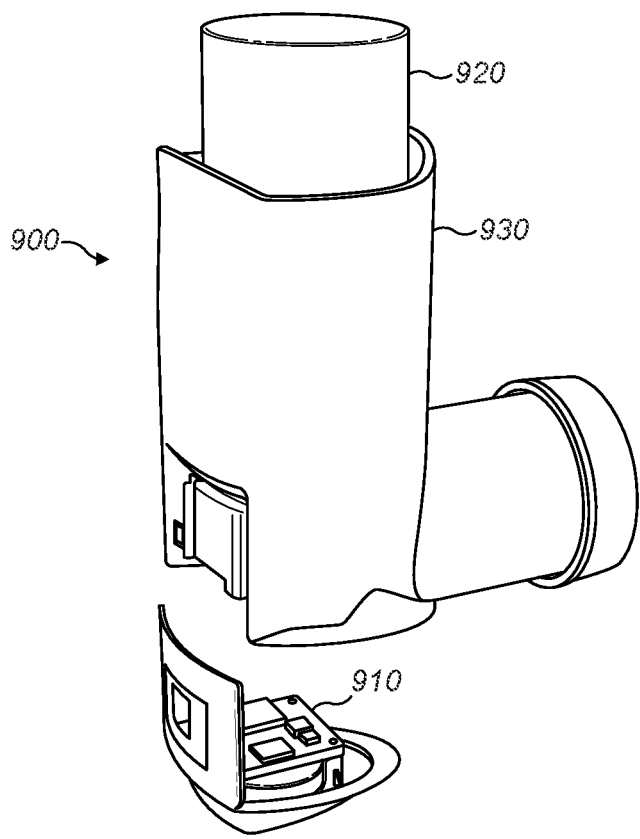
FIG. 9A
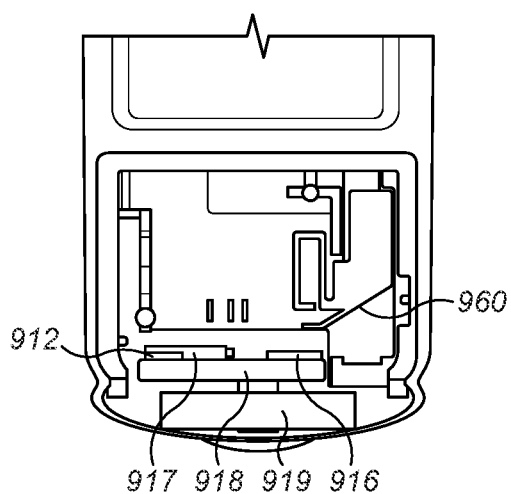 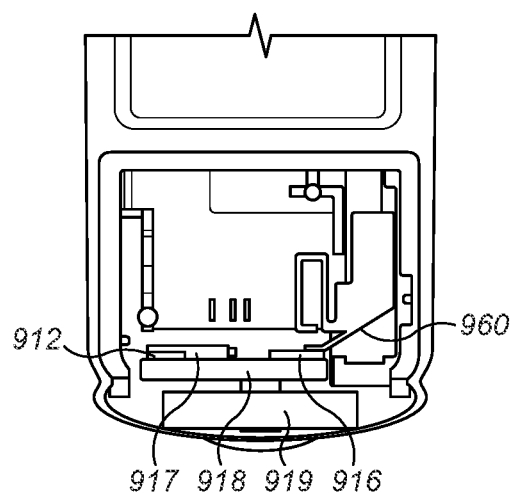
FIG. 9B　　　　　FIG. 9C

COMPLIANCE MONITORING MODULE FOR AN INHALER

This application is a continuation of U.S. patent application Ser. No. 15/507,386, filed Feb. 28, 2017, which is the National Stage Entry under 35 U.S.C. § 371 Patent Cooperation Treaty Application No. PCT/US2015/047369, filed Aug. 28, 2015, which claims the benefit of the United States Provisional Application No. 62/043,114 filed on Aug. 28, 2014, the contents of which are incorporated fully herein by reference in their entirety.

The present disclosure generally relates to monitoring of patient compliance to medicament administration via an inhaler. More particularly, the disclosure relates to the use of a miniature pressure sensor for compliance monitoring in an inhaler.

Inhalers or puffers are used for delivering medication into the body via the lungs. They can be used, for example, in the treatment of asthma and chronic obstructive pulmonary disease (COPD). Types of inhalers include metered dose inhalers (MDIs), nebulisers and dry powder inhalers (DPIs).

MDIs comprise three major components: a canister, which is normally aluminium or stainless steel, where the drug formulation resides; a metering valve, which allows a metered quantity of the formulation to be dispensed with each actuation; and an actuator (or mouthpiece) which allows the patient to operate the device and directs aerosolised drug into the patient's lungs. The formulation itself is made up of the drug, a liquefied gas propellant and, in many cases, stabilising excipients. The actuator contains a mating discharge nozzle and generally includes a dust cap to prevent contamination. To use the inhaler the patient presses down on the top of the canister, with their thumb supporting the lower portion of the actuator. Actuation of the device releases a single metered dose of the formulation which contains the medication either dissolved or suspended in the propellant. Breakup of the volatile propellant into droplets, followed by rapid evaporation of these droplets, results in the generation of an aerosol consisting of micrometre-sized medication particles that are then inhaled.

Jet nebulisers, also known as atomisers, are connected by tubing to a compressor that causes compressed air or oxygen to flow at high velocity through a liquid medicine to turn it into an aerosol, which is then inhaled by the patient. Jet nebulisers are commonly used for patients in hospitals who have difficulty using other inhalers, such as in serious cases of respiratory disease, or severe asthma attacks.

DPIs deliver medication to the lungs in the form of a dry powder. DPIs are commonly used to treat respiratory diseases such as asthma, bronchitis, emphysema and COPD. DPIs may require some procedure to allow a measured dose of powder to be ready for the patient to take. The medication is commonly held either in a capsule for manual loading or in a hopper/reservoir inside the inhaler. Once loaded or actuated, the patient puts the mouthpiece of the inhaler into their mouth and takes a deep inhalation, holding their breath for 5 to 10 seconds.

A common problem faced in respiratory drug delivery, regardless of the device used, is how to monitor patient adherence and compliance.

Adherence deals with the patient following the prescription label, for example taking the prescribed number of doses per day. If the prescription calls for two doses each day, and the patient is taking two doses a day, they are considered 100% adherent. If the patient is only taking one dose a day, they are only 50% adherent. In the latter case, the patient is not getting the treatment prescribed by their doctor.

Compliance, on the other hand, relates to how the patient uses their drug delivery device. If used in the manner recommended for effective treatment, they are 100% compliant. If not used properly however, they are less than 100% compliant.

As one example, consider a patient prescribed a pMDI. Many such devices require the drug canister to be shaken prior to use, in order that the drug and propellant be properly mixed within the canister. This overcomes the so called "creaming effect" that occurs between uses, the phenomenon whereby medication separates from the propellant and floats to the top (i.e. creams).

Without shaking, the patient may receive less than a recommended dose of medicament. Another issue with pMDI devices is the coordinated hand/breath maneuver required to ensure medicament is actually delivered to the lungs. Said requirement involves 1) inhaling and then, while continuing to inhale, 2) dispensing the medicament by pressing down on the canister, followed by 3) continued inhalation, and finally 4) holding of one's breath for a brief period of time. This last step is important for 'sedimentation' of drug to occur within the lungs. The flow rate during inhalation may need to exceed some minimum threshold value for the drug to be delivered effectively. For many patients, compliance to such a multi-step process is not easy, either because they are not familiar with the procedure or, e.g. in the case of children and the elderly, find it difficult to perform.

As another example, most DPIs rely on the force of patient inhalation to entrain powder from the device and subsequently break-up the powder into particles that are small enough to reach the lungs. For this reason, insufficient patient inhalation flow rates may lead to reduced dose delivery and incomplete de-aggregation of the powder, leading to unsatisfactory treatment outcomes. In addition, if a user exhales into the device, some of the dose may be lost to the surrounding air. This both reduces the dose delivered to the patient such that they are not fully compliant, and can pose a risk to others in the vicinity by exposing them to a drug they have not been prescribed.

When a doctor prescribes a medication, the efficacy of that treatment is totally dependent on the patient using their device properly and the proper number of times each day. If they fail to do so, the patient is likely to experience no improvement in their condition. Absent any means of verifying patient adherence/compliance, yet faced with a patient for whom no improvement can be seen, the doctor may have no choice but to prescribe a stronger dose or even a stronger medication. In some cases, this may put the patient at risk. This could be avoided if the doctor had some way of confirming that the patient was actually getting the medication prescribed.

The approach followed by some pharmaceutical companies has been to add integral dose counters to their drug delivery products. For example, a dose counter may be triggered by the press of an actuation button or the opening of a cap or cover. While this provides patients, and caregivers, objective evidence that a device has been handled, it still fails to provide any kind of compliance information. There is no means of determining whether the user has inhaled the entire dose. As such, there is a need for a product that provides not only adherence information, but compliance information as well.

A spirometer is an apparatus for measuring the volume of air inspired and expired by a patient's lungs. Spirometers measure ventilation, the movement of air into and out of the lungs. From the traces, known as spirograms, output by spirometers, it is possible to identify abnormal (obstructive or restrictive) ventilation patterns. Existing spirometers use a variety of different measurement methods including pressure transducers, ultrasonic and water gauge.

In order to monitor the flows associated with breathing, a pressure sensor is most convenient because pressure information can be used to determine flow, which can then be used to determine volume.

Pressure sensors used for breath detection generally measure the pressure difference across a section of the patient airway. This is commonly done using two connections, by tubing or other suitable conduits, to connect the sensor to the airway. It is also possible to use a single connection to the airway, with the other port open to the atmosphere. A single port gauge type sensor can also be used if the pressure within the airway is measured both before and after flow is applied, the difference in readings representing the desired pressure drops across the air path resistance. However, the uncertainty associated with the first (no flow) reading is generally high.

Another problem with conventional pressure sensors is thermal drift; the phenomenon by which the pressure reading can change over time with changes in local temperature. It is possible to compensate for such drift using additional circuitry, but this adds cost and volume and increases power requirements. Such circuitry can be located within the pressure sensor itself, but considering that the sensor is generally somewhat removed from the gas being measured, the temperature detected may not be representative of that gas. The temperature monitoring circuitry could be located at the patient, but this adds additional components, plus cost and complexity.

Yet another problem with conventional pressure sensors is susceptibility to high radio frequency (RF) exposure. This can be a real issue when operating in close proximity to a radio transmitter, such as a mobile phone. Other potential sources include wireless communications devices, such as WI-FI routers and cordless phones, and various other forms of information technology (IT) equipment such as wirelessly networked printers.

Another issue with some conventional pressure sensors is hysteresis, the reluctance of a pressure sensing material such as a diaphragm to return to its original form, shape or position after being deformed. This is observed as a difference in output when passing through the same pressure from different directions (either from above or below the target pressure). When dealing with very low pressure changes, such an offset can be large enough to mask the signal being measured.

There are described herein new means of compliance monitoring.

According to a first aspect, there is provided a compliance monitoring module for an inhaler comprising: a miniature pressure sensor, a sensor port of said sensor being configured to be pneumatically coupled to a flow channel of said inhaler through which a user can inhale; a processor configured to: receive data from a sensing element of the pressure sensor; receive data from a mode sensor configured to detect when the inhaler changes from an inactive mode to an active mode; and based on said data from said pressure sensor sensing element and said data from said mode sensor, compile a compliance report; and a transmitter configured to issue said compliance report.

The miniature pressure sensor could be a microelectromechanical system (MEMS) pressure sensor or a nanoelectromechanical system (NEMS) pressure sensor.

Said mode sensor could be an orientation sensor. Said mode sensor could be a means of determining that the inhaler has been primed for use. Said mode sensor could be one of: an accelerometer, a gyroscope, a mechanical switch, an optical sensor, a Hall effect sensor, a microphone, a temperature sensor and a further pressure sensor.

Where the mode sensor is an accelerometer or a gyroscope, said processor could be further configured to determine an orientation of said inhaler using said accelerometer or gyroscope.

Where the mode sensor is an accelerometer and the inhaler is a jet nebuliser, said processor could be further configured to determine that a compressor of the inhaler has activated based on data received from said accelerometer. Alternatively, where the mode sensor is a further pressure sensor, said processor could be further configured to determine that a compressor of the inhaler has activated based on data received from said further pressure sensor.

Where the mode sensor is an accelerometer and the inhaler is a dry powder inhaler (DPI) configured to receive dry powder medicament stored in capsules, said processor could be further configured to determine that a capsule has been opened and/or vibrated/rotated within a chamber based on data received from said accelerometer.

The compliance monitoring module could be configured to be located entirely within the inhaler in use.

Alternatively, the compliance monitoring module could be configured to be located at least partially external to the inhaler in use.

The compliance monitoring module could further comprise a capillary tube configured for pneumatically coupling said sensor port to said flow channel.

Said capillary tube could comprise a seal between the sensor port and the flow channel, said seal being configured to transfer pressure from the flow channel to the sensor port.

The inhaler could be a pressurised metred dose inhaler (pMDI).

Said flow channel could be a gap between an inhaler boot and a gas canister at least partially received therein.

The compliance monitoring module could be configured to be mounted on a vertical outside edge of the inhaler that is uppermost in use.

The compliance monitoring module could further comprise a lip for clipping the module to the inhaler, configured such that said pneumatic coupling is via a gap between said lip and an interior surface of an outermost wall of said inhaler boot.

The inhaler could be a jet nebuliser.

The compliance monitoring module could be configured to be mounted on an exterior surface of the inhaler that faces substantially away from a patient in use.

The compliance monitoring module could comprise a user interface for indicating that dosing is complete.

The processor could be further configured to determine, from said data from said pressure sensor sensing element, a level of liquid medicament remaining in the nebuliser.

The inhaler could be a dry powder inhaler (DPI).

Said DPI could be configured to receive dry powder medicament stored in capsules.

Said processor could be further configured to determine from said data received from the miniature pressure sensor whether one or more predetermined requirements for successful dosing are met. Said one or more requirements could comprise one or more of: flow rate exceeding a predetermined threshold value; inhalation duration exceeding a predetermined threshold value; flow rate exceeding a predetermined threshold value for at least a predetermined threshold duration; total volume inhaled exceeding a predetermined threshold value; and peak inspired flow (PIF) exceeding a predetermined threshold value.

The module could be configured for use with an inhaler comprising means for user-actuated priming of a dosing mechanism.

Said transmitter could be wireless.

Any two or more of the pressure sensor, processor and transmitter could be comprised in a single integrated circuit or System on Chip (SoC).

The module could further comprise said flow channel, the pressure sensor being located inside the flow channel, the pressure sensor optionally being located in a recess in an internal wall of the flow channel.

The module could further comprise said flow channel, the pressure sensor being located external to the flow channel and said sensor port being pneumatically coupled to the flow channel via an opening in a wall of the flow channel.

The module could further comprise a seal arranged to pneumatically couple the sensor port to said opening, at least a part of said seal optionally being sandwiched between the pressure sensor and the wall, at least a part of said seal optionally extending from an exterior surface of said wall to a surface on which the pressure sensor is mounted so as to encapsulate the pressure sensor in a pneumatic chamber adjacent the wall.

Said wall and said seal could be formed by a two-shot moulding process.

The module could further comprise a thermally conductive gasket sandwiched between the pressure sensor and the wall, said thermally conductive gasket optionally acting as the seal.

The module could further comprise an air-permeable, water-impermeable filter separating said sensor port from said flow channel.

The pressure sensor could comprise a metal housing.

The pressure sensor could be a MEMS barometric pressure sensor. The sensor could be a piezo-resistive or capacitive MEMS pressure sensor.

Said processor could be comprised in the pressure sensor.

The module could further comprise a data buffer configured to store data received from a sensing element of the pressure sensor. Said data buffer could optionally be comprised in the pressure sensor. Said data buffer could be configured to store data corresponding to one inhalation/exhalation waveform. Said data buffer could be a first in, first out (FIFO) data buffer.

The module could further comprise an additional MEMS barometric pressure sensor configured for monitoring environmental barometric activity.

The transmitter could be comprised in a transceiver configured to communicate data from and/or to the pressure sensor. The transmitter could be wireless. Said wireless transmitter could be a Bluetooth™ subsystem, optionally a Bluetooth™ Low Energy (BLE) integrated circuit or System on Chip (SoC).

The pressure sensor and/or the transmitter could be mounted on a printed circuit board (PCB).

The module could further comprise a battery, optionally a coin cell, arranged to power the pressure sensor.

The pressure sensor could have a sensitivity of 20 Pascals or less.

The pressure sensor could comprise a sensing element. The processor could be configured to poll said sensing element at a frequency of greater than or equal to 100 Hz.

The module could further comprise control means for switching on the pressure sensor and/or waking the pressure sensor from a low power state.

Said control means could be a mechanical switch, an optical sensor, an accelerometer or a Hall effect sensor.

The processor could be configured to respond to said control means switching on and/or waking up the pressure sensor by taking a tare reading from said sensing element and calibrating data received from the sensing element subsequently using said tare reading.

The processor could be configured to determine a dynamic zero from a moving average of measurements by the pressure sensor, and dynamically calibrate the pressure sensor according to said dynamic zero.

The processor could be configured to filter out electrical noise inherent to the pressure sensor and/or environmental anomalies in data received from a sensing element of the pressure sensor.

The module could further comprise a temperature sensor, optionally integral with the pressure sensor. The processor, optionally comprised in one of the pressure and temperature sensors, could be configured to apply temperature compensation determined from data received from a sensing element of the temperature sensor to data received from a sensing element of the pressure sensor.

The inhaler could further comprise a mouthpiece, said sensor port being pneumatically coupled to a flow channel in pneumatic communication with said mouthpiece.

According to a second aspect there is provided an inhaler accessory comprising the module of the first aspect, configured to be connected to an inhaler such that said sensor port is pneumatically coupled to a flow channel in pneumatic communication with a mouthpiece of said inhaler.

According to a third aspect there is provided an inhaler comprising the compliance monitoring module of the first aspect.

According to a fourth aspect there is provided a method for monitoring compliance of use of an inhaler comprising: receiving data from a mode sensor configured to detect when the inhaler changes from an inactive mode to an active mode; receiving data from a sensing element of a miniature pressure sensor, a sensor port of said sensor being configured to be pneumatically coupled to a flow channel of said inhaler through which a user can inhale; based on said data from said pressure sensor sensing element and said data from said mode sensor, compiling a compliance report; and issuing said compliance report.

The miniature pressure sensor could be a microelectromechanical system (MEMS) pressure sensor or a nanoelectromechanical system (NEMS) pressure sensor. The pressure sensor could be a MEMS barometric pressure sensor. The sensor could be a piezo-resistive or capacitive MEMS pressure sensor.

If the inhaler is a jet nebuliser, said method could further comprise determining, from said data from said pressure sensor sensing element, a level of liquid medicament remaining in the inhaler.

If the mode sensor is an accelerometer or a gyroscope, said method could further comprise determining an orientation of said inhaler using said accelerometer or gyroscope.

If the mode sensor is an accelerometer or a further pressure sensor and the inhaler is a jet nebuliser, said method could further comprise determining that a compressor of the inhaler has activated using said accelerometer or further pressure sensor.

If the mode sensor is an accelerometer and the inhaler is a dry powder inhaler (DPI) configured to receive dry powder medicament stored in capsules, said method could further comprise determining that a capsule has been opened and/or vibrated/rotated within a chamber using said accelerometer.

Said mode sensor could be an orientation sensor. Said mode sensor could be a means of determining that the inhaler has been primed for use. Said mode sensor could be one of: an accelerometer, a gyroscope, a mechanical switch, an optical sensor, a Hall effect sensor, a microphone, and a temperature sensor.

The method could be performed entirely by the inhaler.

Alternatively, the method could be performed at least partially by apparatus external to the inhaler.

There could be a capillary tube configured for pneumatically coupling said sensor port to said flow channel.

Said capillary tube could comprise a seal between the sensor port and the flow channel, said seal being configured to transfer pressure from the flow channel to the sensor port.

The inhaler could be a pressurised metered dose inhaler (pMDI).

Said flow channel could be a gap between an inhaler boot and a gas canister at least partially received therein.

The method could be performed by a module mounted on a vertical outside edge of the inhaler that is uppermost in use. Said module could further comprise a lip for clipping the module to the inhaler, configured such that said pneumatic coupling is via a gap between said lip and an interior surface of an outermost wall of said inhaler boot.

The inhaler could be a jet nebuliser.

The method could be performed by a module mounted on an exterior surface of the inhaler that faces substantially away from a patient in use.

The method could further comprise indicating, via a user interface, that dosing is complete.

The method could further comprise determining, from said data from said pressure sensor sensing element, a level of liquid medicament remaining in the inhaler.

The inhaler could be a dry powder inhaler (DPI).

Said DPI could be configured to receive dry powder medicament stored in capsules.

Said method could further comprise determining from said data received from said pressure sensor whether one or more predetermined requirements for successful dosing are met. Said one or more requirements could comprise one or more of: flow rate exceeding a predetermined threshold value; inhalation duration exceeding a predetermined threshold value; flow rate exceeding a predetermined threshold value for at least a predetermined threshold duration; total volume inhaled exceeding a predetermined threshold value; and peak inspired flow (PIF) exceeding a predetermined threshold value.

The inhaler could comprise means for user-actuated priming of a dosing mechanism.

Said issuing could be by means of wireless transmission.

Any two or more of the pressure sensor, a processor and a transmitter for performing the method could be comprised in a single integrated circuit or System on Chip (SoC).

The pressure sensor could be located inside the flow channel, the pressure sensor optionally being located in a recess in an internal wall of the flow channel.

The pressure sensor could be located external to the flow channel and said sensor port could be pneumatically coupled to the flow channel via an opening in a wall of the flow channel.

A seal could be arranged to pneumatically couple the sensor port to said opening, at least a part of said seal optionally being sandwiched between the pressure sensor and the wall, at least a part of said seal optionally extending from an exterior surface of said wall to a surface on which the pressure sensor is mounted so as to encapsulate the pressure sensor in a pneumatic chamber adjacent the wall.

Said wall and said seal could be formed by a two-shot moulding process.

There could be a thermally conductive gasket sandwiched between the pressure sensor and the wall, said thermally conductive gasket optionally acting as the seal.

There could be an air-permeable, water-impermeable filter separating said sensor port from said flow channel.

The pressure sensor could comprise a metal housing.

The pressure sensor could be a MEMS barometric pressure sensor. The sensor could be a piezo-resistive or capacitive MEMS pressure sensor.

A processor could be comprised in the pressure sensor.

The method could further comprise storing data received from a sensing element of the sensor in a data buffer. Said data could correspond to one inhalation/exhalation waveform. Said data buffer could optionally be comprised in the pressure sensor. Said data buffer could be a first in, first out (FIFO) data buffer.

The method could further comprise: monitoring environmental barometric activity using an additional MEMS barometric pressure sensor; and calibrating said sensor having the sensor port pneumatically coupled to said flow channel against said additional sensor.

Said issuing could be by means of wireless transmission. Said wireless transmitting could use a Bluetooth™ protocol, optionally the Bluetooth™ Low Energy (BLE) protocol.

The issuing could be by means of a transmitter comprised in a transceiver configured to communicate data from and/or to the pressure sensor. The transmitter could be wireless. Said wireless transmitter could be a Bluetooth™ subsystem, optionally a Bluetooth™ Low Energy (BLE) integrated circuit or System on Chip (SoC).

The pressure sensor and/or the transmitter could be mounted on a printed circuit board (PCB).

The pressure sensor could be powered by a battery, optionally a coin cell.

The pressure sensor could have a sensitivity of 20 Pascals or less.

The pressure sensor could comprise a sensing element. The method could comprise polling said sensing element at a frequency of greater than or equal to 100 Hz.

The method could further comprise using control means to switch on the pressure sensor and/or wake the pressure sensor from a low power state.

Said control means could be a mechanical switch, an optical sensor, an accelerometer or a Hall effect sensor.

The method could further comprise, in response to said control means switching on and/or waking up the pressure sensor, taking a tare reading from said sensing element and calibrating data received from the sensing element subsequently using said tare reading.

The method could further comprise determining a dynamic zero from a moving average of measurements by the pressure sensor, and dynamically calibrating the pressure sensor according to said dynamic zero.

The method could further comprise filtering out electrical noise inherent to the pressure sensor and/or environmental anomalies in data received from a sensing element of the pressure sensor.

The method could further comprise applying temperature compensation to data received from a sensing element of the pressure sensor using data received from a sensing element of a temperature sensor.

The inhaler could further comprise a mouthpiece, said sensor port being pneumatically coupled to a flow channel in pneumatic communication with said mouthpiece.

The method could further comprise determining the volume of air inspired or expired by a user of the inhaler from data sensed by a sensing element of the sensor.

According to a fifth aspect there is provided a computer program product comprising instructions for execution by a computer processor to perform the method of the fourth aspect.

According to a sixth aspect, there is provided a compliance monitoring module substantially as herein described with reference to the accompanying figures.

According to a seventh aspect, there is provided an inhaler accessory substantially as herein described with reference to the accompanying figures.

According to an eighth aspect, there is provided an inhaler substantially as herein described with reference to the accompanying figures.

According to a ninth aspect, there is provided a method substantially as herein described with reference to the accompanying figures.

According to a tenth aspect, there is provided a computer program product substantially as herein described with reference to the accompanying figures.

Examples of the present invention will now be described with reference to the accompanying drawings, in which:

FIGS. 7 to 12 illustrate example configurations of compliance modules in inhalers;

Elements shown in the Figures are not drawn to scale, but only to illustrate operation. Like elements are indicated by like reference numerals.

Figure 1:
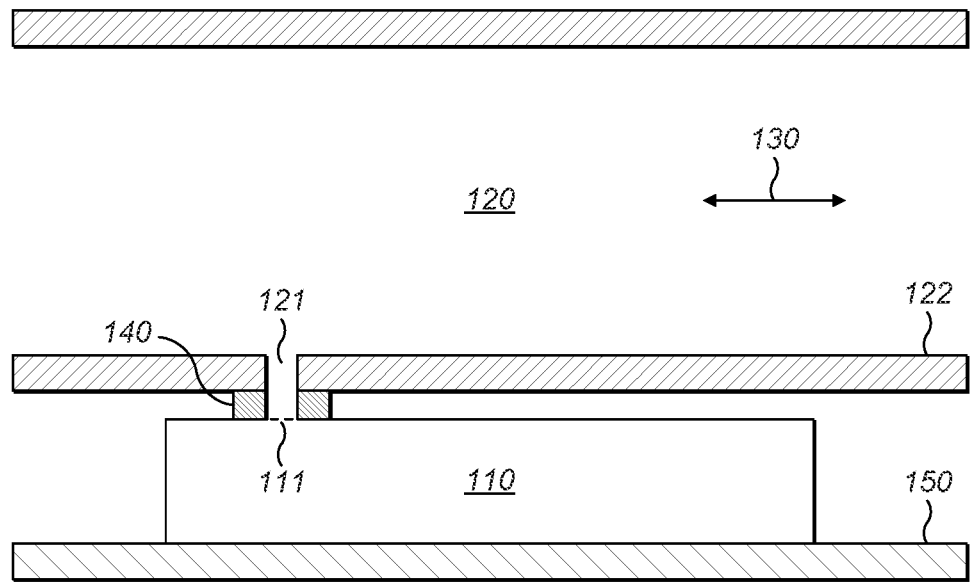
FIGS. 1 to 5 illustrate example arrangements for a miniature pressure sensor for breath detection with respect to a flow channel.

In addition to the differential (two port) type pressure sensors and the single port gauge type sensors, with separate measurements made before and after use, discussed above, absolute or barometric pressure sensors are available. Barometric pressure sensors are referenced to vacuum. They are sometimes referred to as altimeters since altitude can be deduced from barometric pressure readings. Sensors of this type have not generally been considered for use in breath detection because of their extremely wide range (20 to 110 kPa) and low resolution. Considering how a typical breath profile may generate pressure changes of the order of only 0.2 kPa, this would require operating the sensor over an extremely narrow portion of its operating range.

However, with miniaturisation, including the introduction of MEMS and NEMS technologies, much improved sensors are now available. A typical MEMS barometric sensor is capable of operation from 20 kPa to 110 kPa and can detect flow rates of less than 30 lpm (litres per minute) when pneumatically coupled to a flow path having a known flow resistance.

Using a barometric sensor enables use of the barometric pressure as a baseline throughout the measurement cycle, thereby addressing the uncertainty of other single port approaches.

Also, having knowledge of the local barometric pressure can provide some insight into patient lung function. It is suspected that changes in atmospheric pressure, such as those associated with approaching storm fronts, may have an effect on patient breathing, possibly even related to asthma and COPD events.

arometric pressure sensors are already in stressed condition, having an integral reference port sealed within the device under vacuum. This means that they have low hysteresis in the region of interest.

Due to the extremely small size and mass of their sensing elements, MEMS sensors are capable of reacting to extremely small pressure changes. Some are capable of resolving pressure changes as low as 1 Pa.

MEMS pressure sensors can include all of the requisite analogue circuitry within the sensor package. Temperature compensation and/or digital interfaces can also be integrated with the pressure sensor.

For example, the Freescale MPL3115A2 MEMS barometer/altimeter chip (pressure sensor) is digital, using an $I^2C$ interface to communicate pressure information to a host micro-computer.

MEMS pressure sensors can be packaged in metal. This provides RF shielding and good thermal conductivity for temperature compensation.

MEMS pressure sensors are also low cost, exhibit low power consumption and are very small. This makes them especially suitable for use in portable and/or disposable devices which may, for example, be powered by batteries such as coin cells.

The small size of MEMS pressure sensors makes it easy to incorporate them into existing designs of inhalers. It may be easier to incorporate them in or close to a mouthpiece to more accurately measure the pressure change caused by a patient's inhalation or exhalation.

In some device designs, a miniature barometric pressure sensor can be connected directly to the patient airway using only a small hole to the air path which does not require tubing of any kind. This minimizes the possibility of moisture condensation and potential bacterial growth associated with elastomeric tubing. An internal seal, for example a gel seal, can be included to protect the sensor element from contamination.

An example of this type of arrangement is shown in FIG. 1. A miniature barometric pressure sensor 110 is placed against the flow channel 120 through which a patient breathes. Airflow is substantially axial as indicated by arrow 130. The sensor port 111 is sealed in line with an opening 121 in flow channel wall 122 by a pneumatic (airtight) seal 140. (Note that, so long as there is a pneumatic connection between the sensor port and the flow channel, the seal need not be completely airtight.) Sensor port 111 optionally comprises a filter, for example an air-permeable, water-impermeable filter. The flow channel and the seal could be formed by a two-shot moulding process. The pressure sensor 110 can be mounted on a printed circuit board (PCB) 150 to provide connection to power sources and other electronics.

Figure 2:
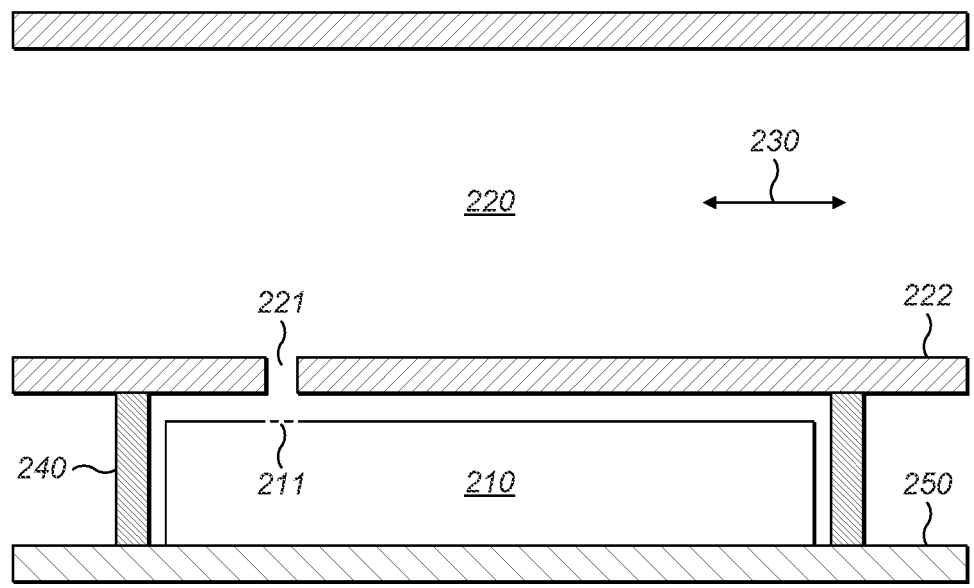

Instead of positioning the seal 140 around the channel between opening 121 and sensor port 111, the entire miniature sensor could be encapsulated within a chamber adjacent to the flow channel as illustrated in FIG. 2. Pneumatic seal 240 is located outside of the sensor footprint and extends all the way from the exterior of flow channel wall 222 to the surface 250 on which the sensor 210 is mounted (for example the component surface of a PCB). FIG. 2 shows a cross-section; pneumatic seal 240 surrounds the perimeter of the sensor 210 whether it is circular, square, rectangular or any other shape. The seal 240, sensor mount 250 and flow channel wall 222 thus form a cavity pneumatically isolated from the external environment except for the flow channel in the location of the opening 221. The pressure at the sensor port 211 is therefore equalised with the pressure in the flow channel at the opening 221.

Since MEMS sensors are available with built-in temperature compensation, there may not be any need for use of external thermal sensors. Compensation can be provided right at the measurement site, increasing the accuracy of the compensation. A MEMS sensor with built-in temperature compensation can also act as a compact breath thermometer, providing further information to the patient and/or their caregiver. If the housing of the sensor is metal, then not only is the sensitive internal circuitry isolated from RF fields, such as those associated with mobile phones or nearby disturbances, but the sensor will also rapidly equilibrate to the local temperature in order to provide optimum temperature compensation.

Figure 3:
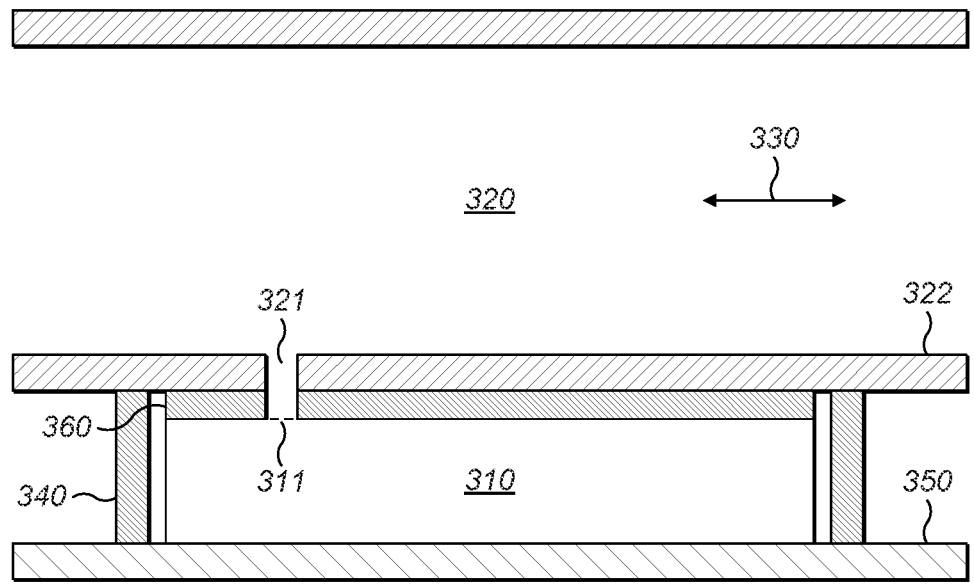

In the embodiments of FIGS. 1 and 2, the miniature sensor is separated from the flow channel wall by an air gap. To improve the ability of the miniature sensor to rapidly detect changes in flow channel temperature, a thermally conductive gasket can be used as shown in FIG. 3. (FIG. 3 is in other respects similar to FIG. 2.)

In the example arrangement of FIG. 3, a thermally conductive gasket 360, such as the silicone types used for transistor heat sinks, is provided between the (optionally metal) housing of the miniature sensor 310 and the flow channel wall 322. The greater the adjacent surface areas covered by the gasket the quicker the temperature equilibration. The gasket 360 could therefore extend over substantially the entire surface of the sensor 310 facing the flow channel wall 322.

Figure 4:
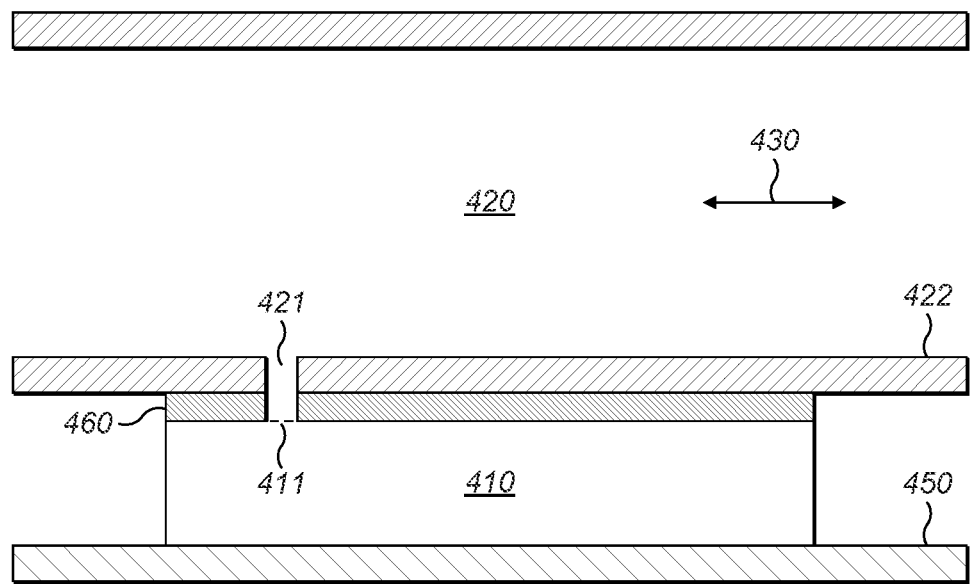

FIG. 4 shows an example arrangement in which a thermally conductive gasket 460 is made of an air-impermeable substance which deforms to the contours of the surfaces of the sensor 410 and flow channel wall 422 it is compressed between. It thus provides a good thermal connection while at the same time acting as a pneumatic seal, eliminating the need for a separate sealing element.

Figure 5:
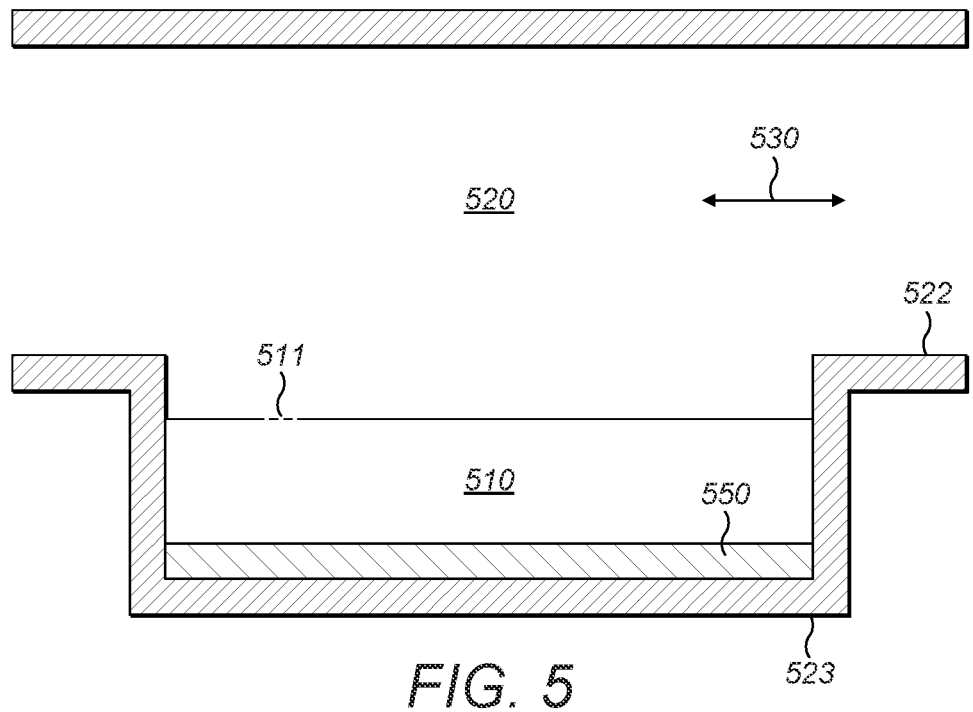

An alternative to positioning the sensor adjacent the flow channel is to place the entire sensor within the low pressure airway of the device to be monitored as illustrated in FIG. 5. For example, the sensor could be placed within the body of a DPI or the 'boot' of a pressurised MDI (pMDI). (The term boot refers to the body of the inhaler that generally holds the drug canister.) in this arrangement the sensor is truly measuring the pressure (and optionally, temperature) of the airflow itself, providing improved accuracy. Therefore there is also no need for any sealing element to create a pneumatic conduit between the flow channel 520 and the sensor port 511, or for any thermally conductive gasket to aid in temperature equilibration between them. It is also not necessary to provide the sensor with any access to the external pressure environment for reference purposes because the reference is already built into the sensor itself in the form of a vacuum reference.

In the example of FIG. 5, the miniature barometric pressure sensor 510 is mounted on the interior of flow channel wall 522, optionally via a PCB 550. The flow channel wall 522 may comprise a recessed part 523 in which the sensor 510 is located as shown to reduce disruption to the airflow indicated at 530. For example, the depth of such a recess 523 could be substantially equal to the thickness of the sensor 510 so that the surface of the sensor comprising the sensor port 511 lies flush with the parts of the interior surface of flow channel wall 522 to either side of the sensor 510. Recess 523 could be a volume cut out of the wall 522 or a part of the wall that extends radially outwards relative to the rest as shown.

It should be noted that due to their small size, miniature pressure sensors can be used to monitor patient flow through, for example, pMDIs, jet nebulisers or DPIs, thus facilitating low cost compliance monitoring, in addition to/in place of adherence monitoring, which confirms device actuation. Said compliance monitoring could be implemented using an accessory device that couples to the dosing device through a small hole to the airway to be monitored, through a capillary tube in fluid communication with the airway to be monitored, or in the dosing device itself. The small size, high performance and low cost of MEMS sensors make them ideally suited to such applications where size and weight are major considerations for users who may have to carry their inhaler with them at all times.

If output from the miniature pressure sensor is digital, all low level signal processing can be done within the sensor, shielding it from outside interference. This makes it possible to work with signals of the order of tens of Pascals without much difficulty, something that traditional sensors with external circuitry would be challenged to do.

Figure 6:
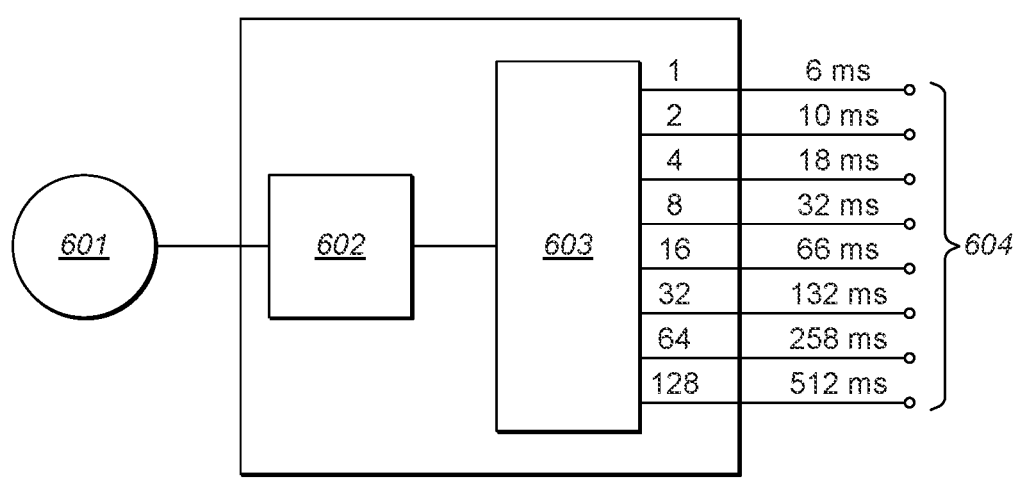
FIG. 6 is a schematic of example sensor electronics.

FIG. 6 shows schematically some electronic components of an example MEMS barometric pressure sensor. Sensor element 601 passes analogue signals to analogue to digital converter (ADC) 602. The digital output signal of ADC 602 is then averaged by a rolling average filter over many cycles to reduce noise. Various averages can be selected under program control in order to balance noise against response time.

As one example, block 603 represents a means of selecting one of eight different oversample (i.e. filter) ratios to output at 604. The fastest response is associated with OSR=1, but this is also the noisiest setting. Conversely, OSR=128 introduces the least noise, but has the slowest response. The optimum setting can be chosen depending on the particular application. With an OSR setting of 16, the output is clean enough and the update time quick enough for most respiratory applications.

It may be desired, for example in order to record patient flow profiles, to create a waveform associated with the real time fluctuations of pressure detected by the sensor. If one were to construct such a waveform from single readings of the sensor each time new data became available, the resulting waveform would exhibit blocky artefacts, rather than a smooth waveform, due to the delays associated with each tap. However, by driving the ADC 602 at a suitable frequency, for example approximately 100 Hz, and reading data at the same rate, the data presented to each tap is further averaged, resulting in a much smoother waveform.

The averaged output can then be passed to a circular first in, first out (FIFO) buffer (not shown) for storage until the data can be processed by a connected processor integrated into the device, or transmitted for offloaded processing. Such a FIFO buffer could, for example, store a number of samples approximately equivalent to, or a little greater than, one typical breath waveform to ensure that an entire inhalation/exhalation profile can be captured. Using a buffer reduces the demand on the serial port of the sensor in cases where the waveform is not required in real time.

With the addition of communications it is possible to monitor patient adherence and compliance and communicate such information, for example including patient flow profiles, to a user device such as a smart phone or tablet. From a user device data can optionally be communicated to a caregiver's device, for example a doctor's personal computer (PC). This could be done using a wired connection, for example via a Universal Serial Bus (USB) port. Alternatively, using wireless technology, it is possible to communicate results to the outside world without interrupting the product housing in any significant way. Suitable wireless technologies could include, for example, WIFI technologies such as IEEE 802.11, Medical Body Area Network (MBAN) technologies such as IEEE 802.15, Near Field Communication (NFC) technologies, mobile technologies such as 3G and Bluetooth™ technologies such as Bluetooth™ Low Energy (BLE). A wireless transceiver, for example in the form of a BLE chip, could be connected to the miniature pressure sensor or integrated with it.

Such wireless connectivity could be used, for example, to report device actuation and/or sensed inhalation with date and time stamps in real time. This data could be processed externally and if the result of such processing is that it is determined that the patient is not fully compliant or that a prescription should be refilled, an alert can be sent to the patient and/or caregiver and/or pharmacist. Alerts could be provided via one or more user interfaces of the inhaler (for example an LED and/or a buzzer) or via text message or email. As another example, if no dosing report is received within a predetermined period following a scheduled dosing time, a reminder could be sent to the patient and/or caregiver. Alerts could also be generated for example if use frequency is exceeding a safe threshold.

The compliance module could communicate directly or indirectly with one or more of: a user device (such as a mobile phone e.g. a smartphone, a tablet, a laptop or a desktop computer) of a patient, or of a caregiver (such as a doctor, nurse, pharmacist, family member or carer), a server e.g. of a health service provider or inhaler or drug manufacturer or distributor or a cloud storage system. Such communication could be via a network such as the internet and may involve a dedicated app, for example on the patient's smartphone.

Compliance monitoring means (such as one or more sensors, e.g. a device actuation sensor such as a mechanical switch, an orientation sensor to check the device is in the proper orientation for efficient dosing such as an accelerometer or a gyroscope and a miniature pressure sensor to detect sufficient flow for proper dose delivery) and compliance reporting means (such as a wireless transmitter or wired output port) could be included in a single module. This module could be sold as a separate inhaler accessory/upgrade for attachment to an existing or slightly modified design of inhaler. Alternatively, the compliance monitoring module could be incorporated into the inhaler during manufacture. It is not required for all components of the compliance monitoring module to be comprised in a single physical unit, though this may be the case (for example the electronic components could all be mounted on a single PCB or even incorporated into a single integrated circuit). In the case of an inhaler accessory version, the module could consist of one or more attachable units. In the case of a module incorporated into an inhaler, the individual components could be located in any suitable locations in or on the inhaler and need not be grouped together or connected any further than required for them to function.

The sensors may communicate with the processor and transmitter by wired or wireless means. For example, if all three are mounted on a single PCB, the sensor port of the miniature pressure sensor may be directly pneumatically coupled to the flow channel by means of a vent or may be indirectly coupled by means of a capillary tube. (If a capillary tube is used a pressure-transferring seal could close the flow channel end of the tube to avoid drug and/or moisture entering the tube and damaging the pressure sensor, blocking the tube or affecting the hygiene of the device.) Alternatively, the miniature pressure sensor could be located within the flow channel itself and communicate wirelessly with one or more of the other compliance module components located in or on another part of the inhaler. With the miniaturisation of electronic components, it may be possible to locate the entire compliance module within the flow channel without obstructing the flow.

The compliance monitoring module could, for example, be used in the types of pMDIs described in U.S. Pat. No. 6,446,627 or U.S. patent application publication Ser. No. 13/110,532. These inhalers comprise dose counters for monitoring adherence. For example, in US 2011/0283997 a spooled ribbon marked with numerals to indicate the number of does remaining is driven to unwind by a ratchet wheel in turn driven by an actuator pawl actuated by movement of the canister.

However, these inhalers do not comprise any means of determining whether the dose has been successfully administered. The addition of a miniature barometric pressure sensor anywhere in the airflow path through the inhaler or anywhere in fluid communication with the airflow path could enable compliance monitoring since such a miniature sensor could collect sufficient data to indicate whether or not the patient inhaled in an appropriate manner (e.g. hard enough and for long enough) to receive a full dose of medicament.

This information, combined with a signal originating from the dose counter mechanism is sufficient to confirm that a dose has been successfully administered.

A signal could be obtained from the dose counter system in any convenient manner. For example, an electronic switch could be arranged such that it is actuated by motion of the pawl or rotation of the spool. This switch could be connected to an input of the processor such that the processor receives an electronic pulse when a dose is metered. Since dose count will be available electronically, the ribbon could be omitted.

Figure 7:
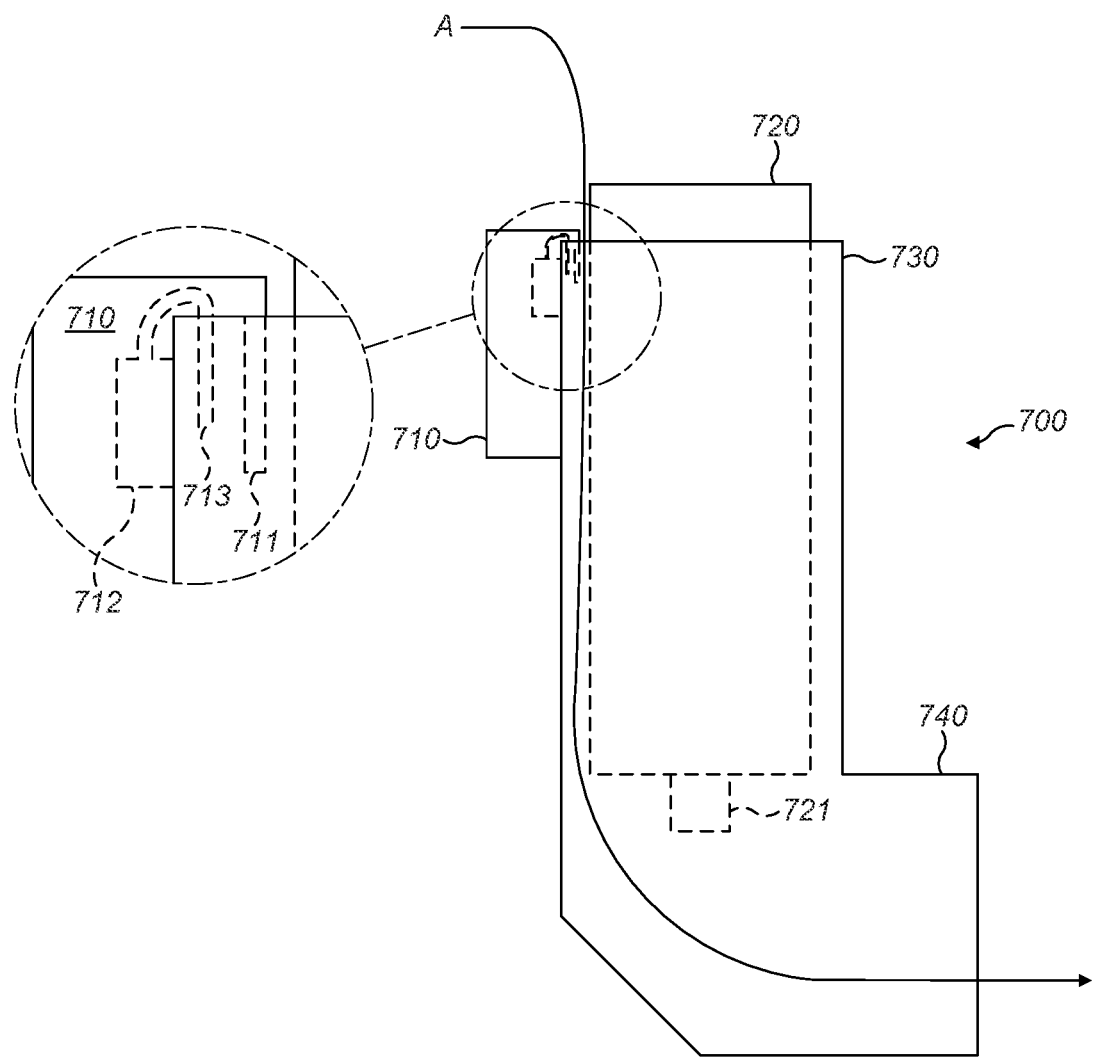
Figure 8:
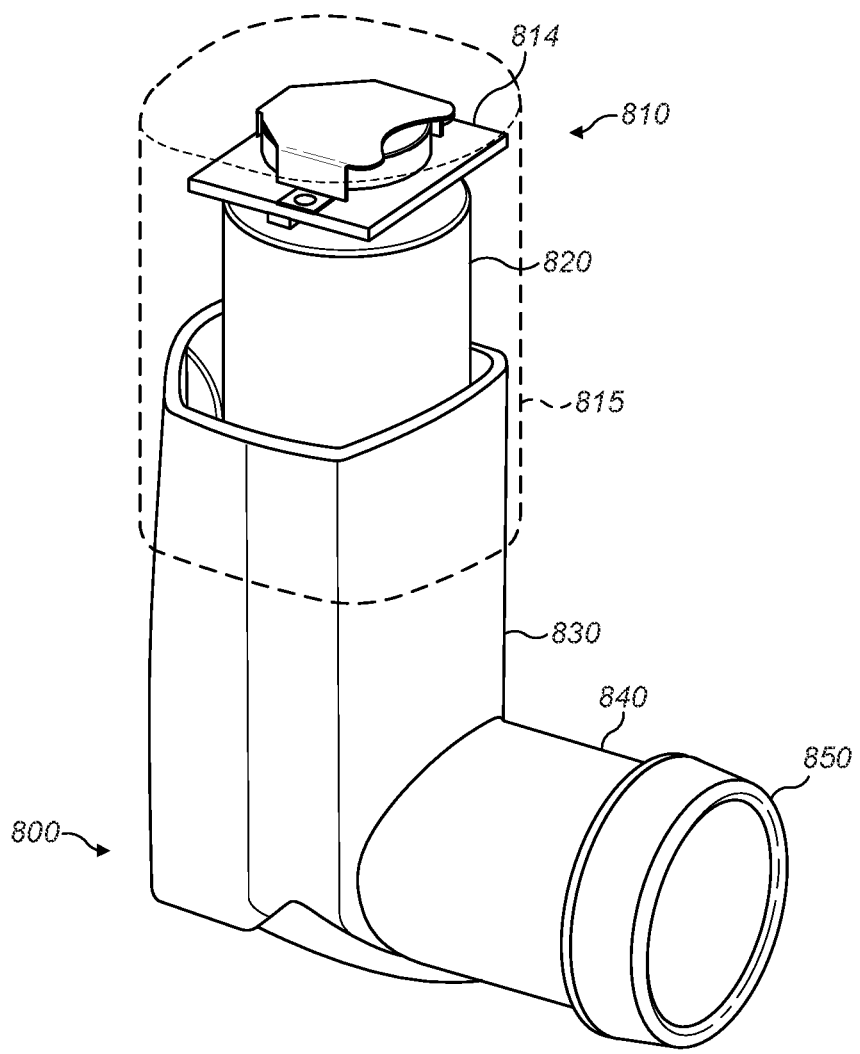
Figure 10A:
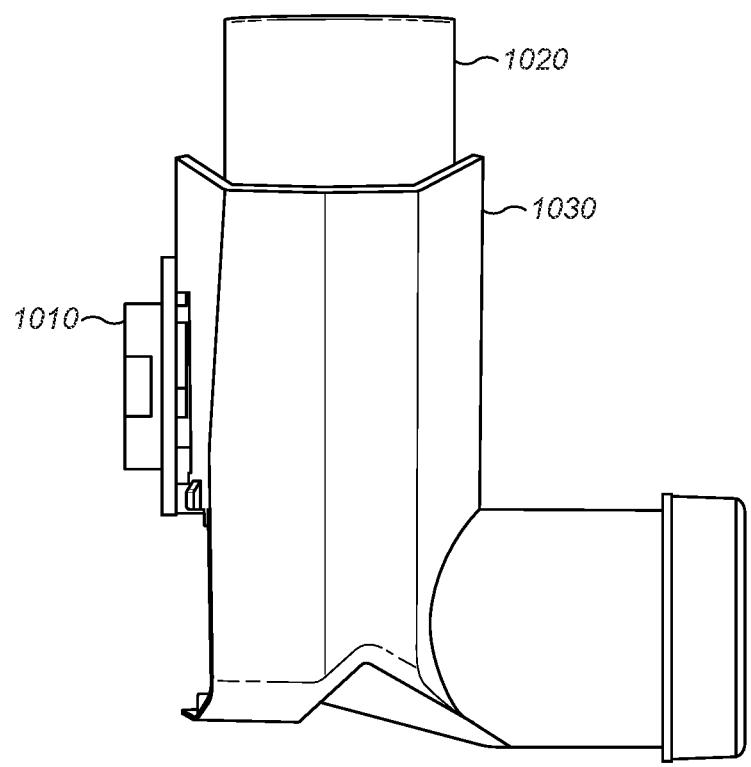
Figure 10B:
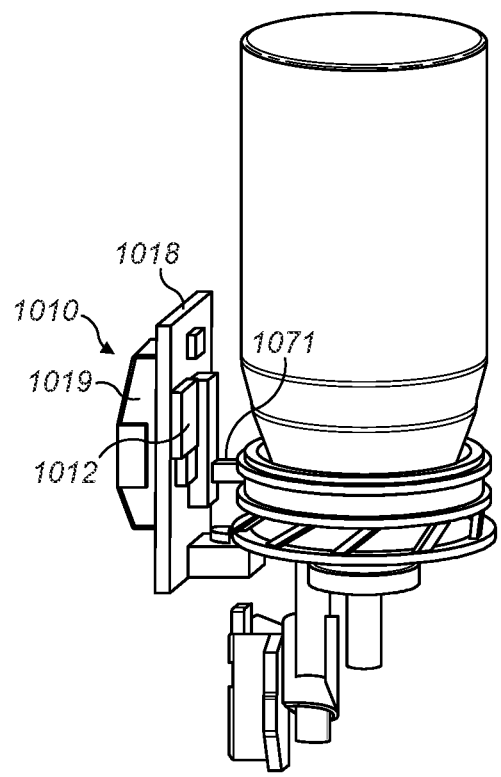

FIGS. 7 to 10 illustrate further details of how a compliance module could be integrated into a pMDI. FIGS. 7 and 8 illustrate how compliance modules could be added to an existing pMDI without any modification, and could therefore be provided separately from the pMDI itself as an accessory/upgrade pack. FIGS. 9 to 10 illustrate how compliance modules could be integrated in pMDIs with some minor modifications.

FIG. 7 illustrates an example in which a compliance module 710 is clipped on to a pMDI 700. pMDI 700 comprises a canister 720 received in a boot 730. A lip 711 of the compliance module hooks over the top of the boot wall in the radial gap between the boot wall and the canister. The compliance module is thereby clipped onto the inhaler without any modification to the inhaler. Arrow A shows the airflow when a user inhales through mouthpiece 740. Air passes down the radial gap between the canister and the boot, entrains aerosol sprayed from nozzle 721 on device actuation, and passes out into the user's mouth through mouthpiece 740. A MEMS pressure sensor 712 in the compliance module is pneumatically coupled to the flow channel formed by the radial gap between the boot and the canister by a capillary tube 713. The capillary tube follows the line of the external wall of the lip round into the gap but stops short of the bottom of the lip. This ensures that the lip blocks all air to the capillary tube except for that from below, i.e. within the boot. In an alternative arrangement, the lip could be shaped and positioned to provide sufficient fluid isolation such that no tube is needed.

An alternative arrangement is shown in FIG. 8 where a compliance module 810 comprises an electronics unit 814 (including a MEMS pressure sensor) affixed to the underside of a cover 815. This all slips over the top of pMDI 800 surrounding the upper section of the boot 830 and the exposed part of the canister 820. With the compliance module in place and dust cap 850 removed, when a user inhales through mouthpiece 840 air flows in through the gap between cover 815 and boot 830, past electronics unit 814 including the MEMS pressure sensor, down the radial gap between the boot and canister, entrains aerosol sprayed from the canister nozzle on device actuation, and passes out into the user's mouth through mouthpiece 840.

FIG. 9A is a partially exploded view of an example pMDI 900 comprising a compliance module 910 incorporated into the bottom of the boot 930. FIGS. 9B and 9C are interior views of the bottom part of the boot respectively before and during device activation. Compliance module 910 comprises MEMS pressure sensor 912, mechanical click dome switch 916 and processor (e.g. microcontroller unit, MCU) 917 mounted on PCB 918 and powered by coin cell battery 919. Before device actuation there is a gap above the upper click dome surface. During device activation the canister 920 is pushed down further into boot 930. A spring arm 960 affixed to the bottom of canister 920 consequently also moves down and pushes down on the upper surface of click dome 916, actuating the switch. This results in an actuation pulse signal being sent to the MCU. This signal can be used to determine patient adherence, while a signal sent from the pressure sensor to the MCU can be used to determine compliance. An accelerometer (e.g. a three-axis accelerometer) could also be provided on the PCB and connected to the MCU to provide compliance data indicating whether the inhaler was shaken before use if required. The accelerometer could also be used to sense the orientation of the inhaler during loading of a dose into the metering chamber to determine whether the inhaler is held upright as required for proper loading. The click dome switch could also act to connect the battery to the pressure sensor or, if no accelerometer is present, to the whole PCB. This would save battery power for only when it is needed. A thermistor could also be included on the PCB, providing further compliance data by indicating whether the temperature drop associated with completion of drug aerosolising occurs.

The compliance module could alternatively be provided as a 'backpack' as shown in FIG. 10. Compliance module 1010 is affixed to the exterior of the boot 1030. A hole in boot 1030 provides fluid communication between the port of a MEMS pressure sensor 1012 and the flow channel formed in the radial gap between the boot 1030 and canister 1020. The sliding contact 1071 of a linear potentiometer 1070 is affixed to the canister such that it moves up and down with the canister. The contact 1071 slides in a slit in the boot 1030. The signal from the potentiometer indicates when the device is actuated and how long it is actuated for. The potentiometer could also act a switch to connect coin cell battery 1019 to PCB 1018 so that the PCB is only powered when the device is being actuated. The slit in which the contact 1071 slides could also provide fluid communication between the flow channel and the MEMS pressure sensor.

Figure 11:
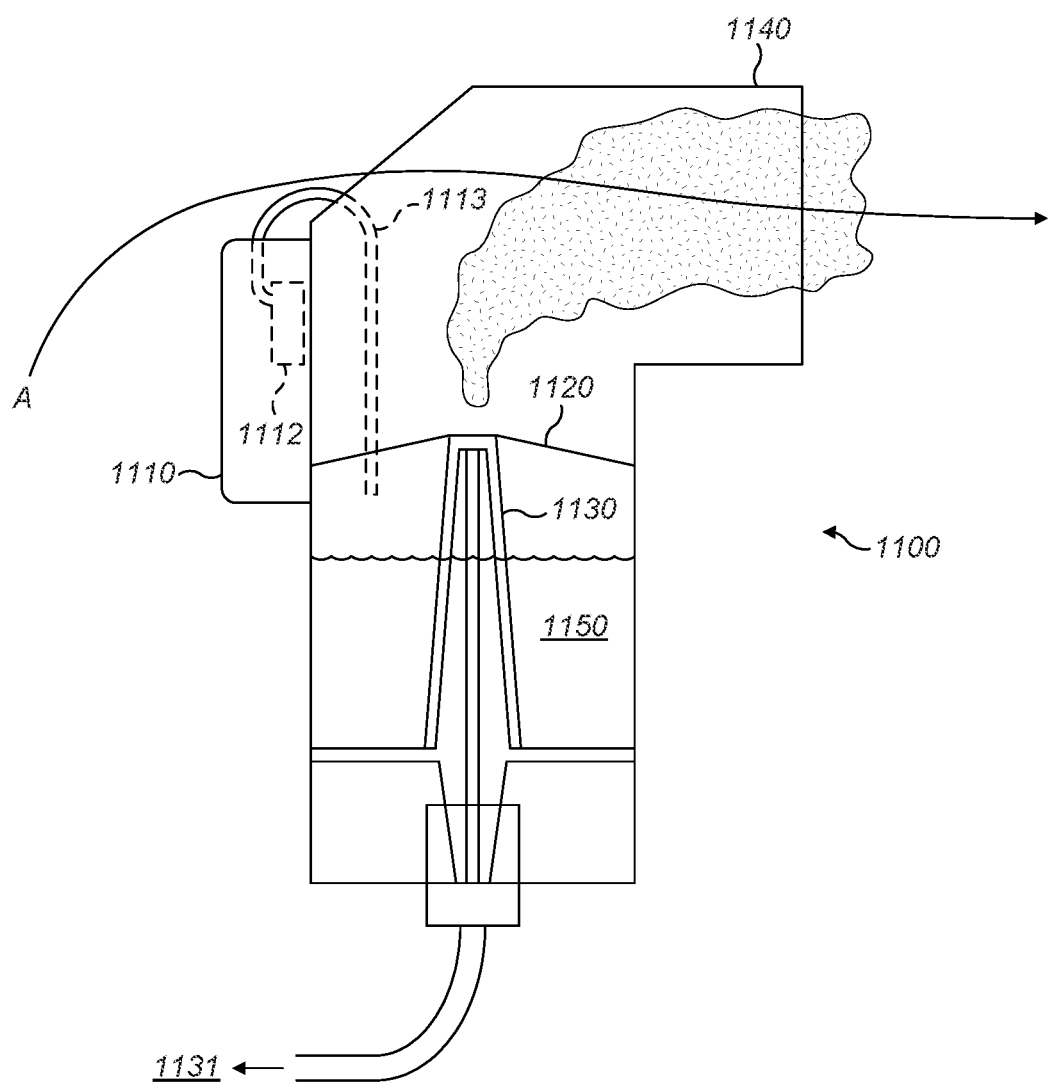

Compliance monitoring modules could also be used in jet nebulisers. FIG. 11 illustrates how this could be achieved. A compliance module 1110 comprising a MEMS pressure sensor 1112 is affixed to the exterior of a jet nebuliser 1100. The sensor port of the pressure sensor communicates with the interior of the nebuliser by means of a capillary tube 1113. The distal end of the tube extends down through a baffle 1120. Baffle 1120 is a flat plate which large aerosol droplets emitted by nozzle 1130 (powered by compressed air inlet 1131) reflect off of such that droplets exiting mouthpiece 1140 into the user's airway are of a uniform size. Locating the end of the capillary tube below the baffle prevents aerosol droplets from entering the tube; provided the nebuliser handset is not shaken so much that liquid medicament from reservoir 1150 splashes up into it, the interior of the tube should remain fairly dry.

Since the baffle is perforated, the pressure above and below it is equalised so the pressure sensor effectively measures the pressure in the mouthpiece 1140. The airflow in the mouthpiece comprises a stream drawn in by user inhalation through vents indicated by arrow A, and a stream emitted by the nozzle. Thus, monitoring the pressure in the mouthpiece can provide both information about patient inhalation and information about the compressor, liquid drug level etc. This could enable feedback to the patient to indicate that treatment is complete or that the reservoir is empty. Patient adherence is often poor with jet nebulisers since the long treatment time (typically of the order of ten minutes) and high noise levels caused by the compressor and handset make it difficult for users to know when the treatment is complete. Thus, use of the compliance monitoring module could improve adherence. The pressure sensor could also be used to check pump function, and as a switch to wake up the rest of the compliance module when one of the large pulsations created by the pump is detected.

An accelerometer could also be included in the compliance monitoring module. For full compliance, some jet nebulisers require the user to tap the handset to shake liquid droplets that have condensed in the mouthpiece back into the reservoir. An accelerometer could detect this tap. An accelerometer could also detect vibrations caused by the compressor to confirm that it is in use.

Figure 12:
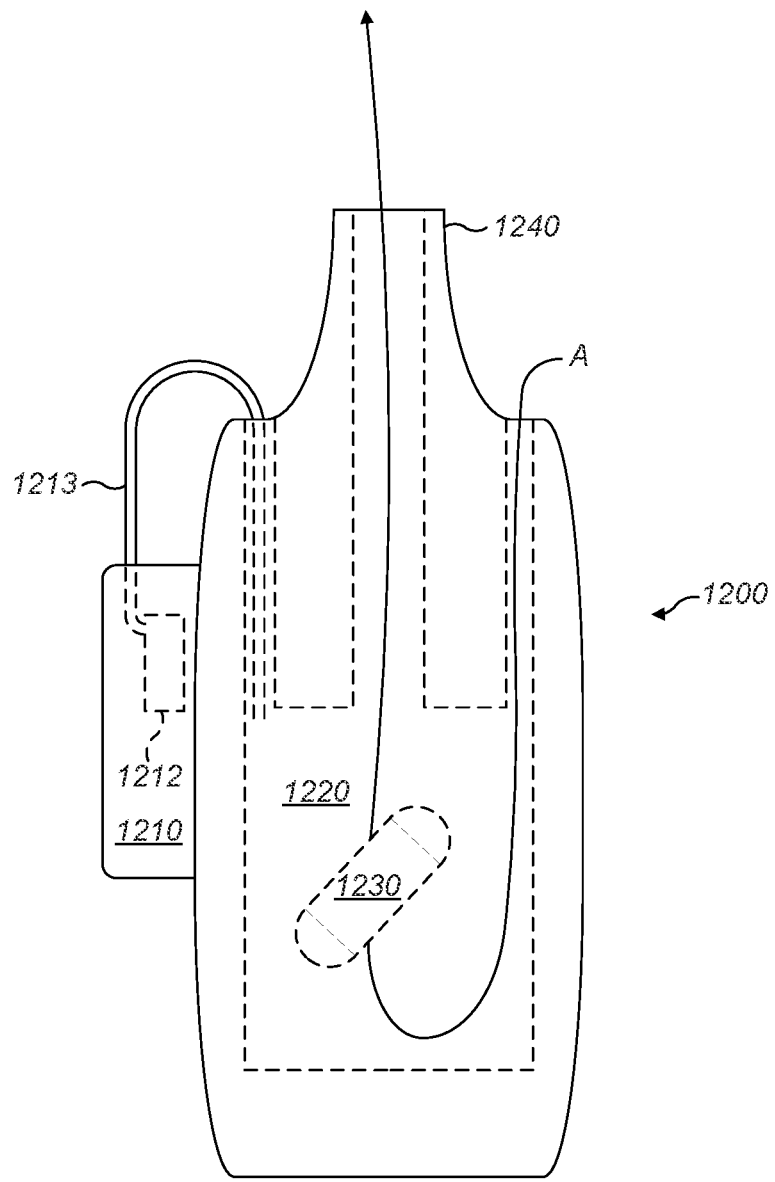

Dry powder inhalers could also benefit from the addition of compliance monitoring modules. An example DPI 1200 with a compliance monitoring module 1210 affixed thereto is shown in FIG. 12. Patient airflow is again shown by arrow A. It passes in through a vent in the inhaler body, passes through a dosing chamber 1220 comprising a medicament capsule 1230 (which has previously been pierced) and then passes out through mouthpiece 1240. The compliance module comprises a MEMS pressure sensor 1212 with a sensor port in fluid communication with the dosing chamber via a capillary tube 1213. An accelerometer or microphone could be included to detect structure-borne vibrations generated by movement of capsule 1230 within chamber 1220 during inhalation. A mechanical switch which feeds back compliance data to a compliance module processor could be actuated by a piercing or peeling mechanism (not shown) which primes the inhaler for use by opening the capsule 1230.

It should be noted that because MEMS barometric pressure sensors respond to environmental barometric pressure, which can change over time, attention should be paid to the initial reading that any subsequent sensor output signal analysis is based upon. An automatic zero reading (i.e. tare) could be performed immediately prior to monitoring any inhalation signal. While it is possible for this value to change over time in response to changes in local environmental barometric pressure, it would not be expected to cause any issues if a treatment is completed within a few minutes. Alternatively, a second barometer chip could be used to keep track of barometric activity, allowing the primary chip to be used exclusively for breath detection.

In a jet nebuliser, the point at which dosing is complete (i.e. where lung volume peaks), could correspond to the point at which flow reverses direction. Thus, the processor can make a determination that dosing is complete when the data from the pressure sensor indicates that flow direction has reversed.

Not all processing needs to be done by the module. Any or all processing could be offloaded to an external data processing device. A wireless scheme (for example comprising a BLE module) could be used to transmit patient flow profiles to an app which could then calculate specific breathing parameters. The inhaler could thereby offload the processing required for such a task to, for example, a smart phone processor. This would facilitate the smallest form factors possible for the inhalers. A further advantage of this approach is that software running on a smart phone can be changed more readily than software running on an inhaler.

Figure 13:
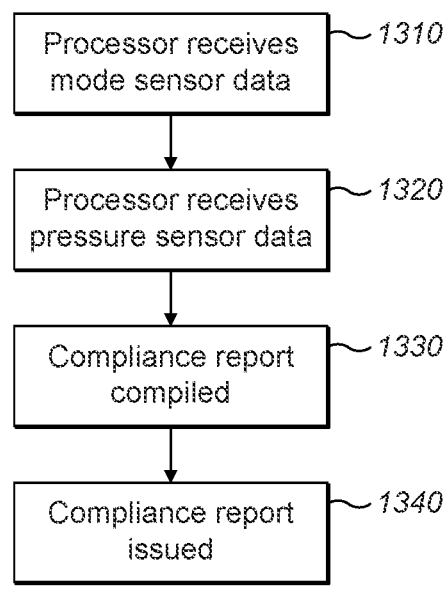
FIG. 13 is a flowchart illustrating an example compliance monitoring method.

FIG. 13 is a flowchart illustrating an example compliance monitoring method. At step 1310 a processor receives data from a mode sensor indicating that the inhaler has changed from being in an inactive mode to an active mode. At step 1320 the processor receives data from a sensing element of a miniature pressure sensor, a sensor port of said sensor being configured to be pneumatically coupled to a flow channel of said inhaler through which a user can inhale. At step 1330 the processor processes the data from the mode sensor and the pressure sensor in order to compile a compliance report. At step 1340 the processor passes the compliance report to a transmitter by which it is issued.

Figure 14A:
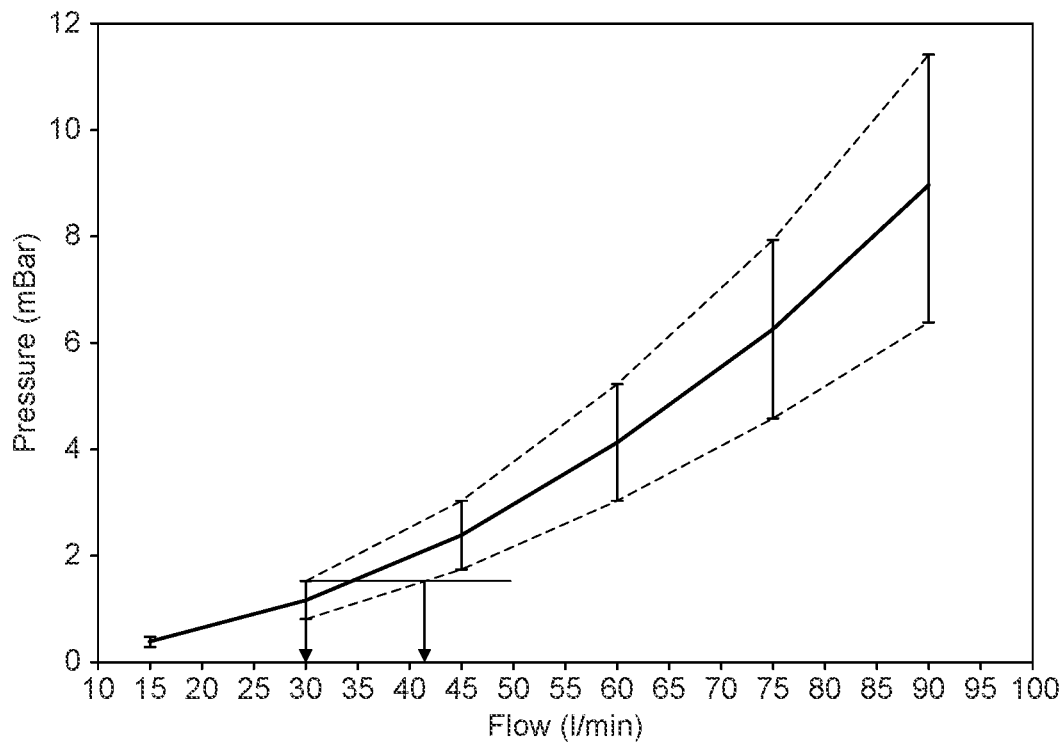
FIGS. 14A and 14B are graphs showing test data.
Figure 14B:
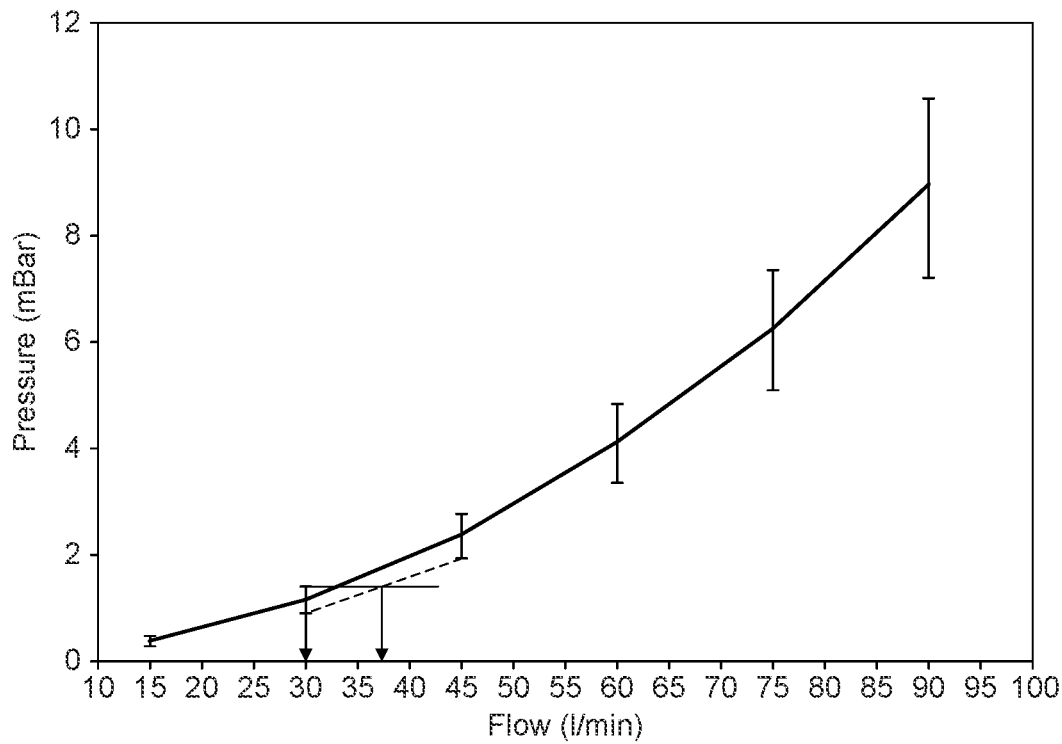

FIGS. 14A and 14B show the mean pressures measured using a miniature relative pressure sensor affixed to the upper part of the casing of 10 different inhalers versus a series of air flow rates applied through the device. Repeat measurements were included for start, middle and end of life of each inhaler (in terms of progress through the number of "shots" before the doses run out). In FIG. 14A, error bars are shown for a +/−3 sigma variation. In FIG. 14B, error bars are shown for a +/−2 sigma variation, capturing a band that 95% of inhalers would fall into. We can thus get an idea of flow uncertainty for pressure measurements by such a sensor used in an inhaler.

For typical inhalation flow rates (30-60 l/min), the uncertainty can be calculated from FIG. 14A as 16 l/min. (The uncertainty in flow rate for each measurement can be estimated as the flow axis differential between the top of the error bar for the measurement and the point at which a line joining the bottoms of the error bars for that measurement and the next reaches the measured pressure. So, for the 30 l/min measurement, the differential is ~41 l/min minus 30 l/min=11 l/min. For 45 l/min the differential is 15 l/min and for 60 l/min it is 22 l/min.) The equivalent value taken from FIG. 14B is ~10 l/min. Sufficient precision can thus be obtained to provide useful compliance data.

The above description relates to exemplary uses of the invention, but it will be appreciated that other implementations and variations are possible.

In addition, the skilled person can modify or alter the particular geometry and arrangement of the particular features of the apparatus. Other variations and modifications will also be apparent to the skilled person. Such variations and modifications can involve equivalent and other features which are already known and which can be used instead of, or in addition to, features described herein. Features that are described in the context of separate embodiments can be provided in combination in a single embodiment. Conversely, features which are described in the context of a single embodiment can also be provided separately or in any suitable sub-combination.

What is claimed is:

1. A pressurized metered dose inhaler (pMDI) comprising:
    a boot-shaped housing;
    a medication reservoir comprising medicament, wherein the medication reservoir is housed within the boot-shaped housing;
    a top cover configured to be attached to an upper section of the boot-shaped housing; and
    a monitoring module located between an underside of the top cover and a top of the medication reservoir, the monitoring module comprising:
        a pressure sensor comprising a sensor port, wherein the sensor port is configured to be pneumatically coupled to a flow channel of the inhaler through which a user can inhale;
        a processor configured to receive data from the pressure sensor; and
        a wireless transmitter configured to transmit the data to a user device; and
    wherein the pressure sensor, the processor, and the wireless transmitter are located between the underside of the top cover and the top of the medication reservoir.

2. The inhaler of claim 1, wherein the top cover is configured to conceal a top side of the medication reservoir.

3. The inhaler of claim 2, wherein the monitoring module is affixed to the underside of the top cover.

4. The inhaler of claim 2, wherein the top cover is removable from the boot-shaped housing.

5. The inhaler of claim 1, wherein the monitoring module further comprises an electronic switch that is configured to be actuated when a dose of medicament is metered from the inhaler.

6. The inhaler of claim 1, wherein the monitoring module further comprises a mechanical switch configured to determine that the inhaler has been primed for use.

7. The inhaler of claim 1, wherein the monitoring module further comprises an orientation sensor, and wherein the processor is further configured to determine that the inhaler has been primed for use based on feedback from the orientation sensor.

8. The inhaler of claim 1, wherein the pressure sensor comprises a barometric pressure sensor.

9. The inhaler of claim 8, wherein the monitoring module further comprises a switch that is configured to wake the pressure sensor from a low power state, wherein the monitoring module is configured to take a tare reading after waking from the low power state.

10. The inhaler of claim 1, wherein the monitoring module further comprises a temperature sensor, and wherein the processor is configured to receive data from the temperature sensor and the wireless transmitter is configured to transmit the data from the temperature sensor to the user device.

11. The inhaler of claim 1, wherein the monitoring module further comprises an optical sensor that is configured to determine whether the inhaler has been primed for use.

12. The inhaler of claim 1, wherein the data comprises an indication of an actuation of the inhaler and sensed inhalation data with associated time stamps.

13. The inhaler of claim 1, wherein the monitoring module is further configured to determine whether one or more predetermined requirements for successful dosing are met based on the data received from the pressure sensor, wherein the one or more predetermined requirements comprise one or more of:
- a flow rate exceeding a predetermined threshold value;
- an inhalation duration exceeding a predetermined threshold value;
- a flow rate exceeding a predetermined threshold value for at least a predetermined threshold duration;
- a total volume inhaled exceeding a predetermined threshold value; or
- a peak inspired flow (PIF) exceeding a predetermined threshold value.

14. The inhaler of claim 1, further comprising a light emitting diode (LED), wherein the processor is configured to generate an alert using the LED to indicate a user's non-compliance with a dosing regimen of the inhaler or to provide a dose reminder to the user of the inhaler.

15. The inhaler of claim 1, wherein the medication reservoir comprises beclomethasone dipropionate.

16. A system comprising:
a user device comprising a processor; and
a pressurized metered dose inhaler (pMDI) comprising:
- a boot-shaped housing;
- a medication reservoir comprising medicament, wherein the medication reservoir is housed within the boot-shaped housing;
- a top cover configured to be attached to an upper section of the boot-shaped housing; and
- a monitoring module located in a space between an underside of the top cover and a top of the medication reservoir, the monitoring module comprising:
  - a sensor comprising a sensor port, wherein the sensor port is configured to be pneumatically coupled to a flow channel of the inhaler through which a user can inhale;
  - a processor configured to receive data from the sensor; and
  - a wireless transmitter configured to transmit the data to the user device; and
wherein the processor of the user device is configured to process the data from the sensor and determine, based on the data, whether one or more predetermined requirements for successful dosing are met.

17. The system of claim 16, wherein the top cover is configured to conceal a top side of the medication reservoir, and wherein the monitoring module is affixed to the underside of the top cover.

18. The system of claim 16, wherein the sensor comprises a pressure sensor; and
wherein the monitoring module further comprises a switch that is configured to wake the pressure sensor from a low power state, and the monitoring module is configured to take a tare reading after waking from the low power state.

19. The system of claim 16, wherein the processor of the user device is configured to determine, based on the data, that successful dosing is met when an inhalation duration exceeds a predetermined threshold value, when a flow rate exceeds a predetermined threshold value for at least a predetermined threshold duration, when a total volume inhaled exceeds a predetermined threshold value, or when a peak inspired flow (PIF) exceeds a predetermined threshold value.

* * * * *